(12) United States Patent
Fahim et al.

(10) Patent No.: US 10,413,363 B2
(45) Date of Patent: Sep. 17, 2019

(54) AUGMENTED REALITY SOLUTION TO OPTIMIZE THE DIRECTIONAL APPROACH AND THERAPY DELIVERY OF INTERVENTIONAL CARDIOLOGY TOOLS

(71) Applicant: Medtronic, Inc., Minneapolis, MN (US)

(72) Inventors: Mina S. Fahim, New Brighton, MN (US); Peter N. Braido, Linwood, MN (US); Ross D. Hinrichsen, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 6 days.

(21) Appl. No.: 15/843,341

(22) Filed: Dec. 15, 2017

(65) Prior Publication Data
US 2019/0183577 A1    Jun. 20, 2019

(51) Int. Cl.
*A61B 34/10* (2016.01)
*A61B 17/34* (2006.01)
(Continued)

(52) U.S. Cl.
CPC .............. *A61B 34/10* (2016.02); *A61B 5/044* (2013.01); *A61B 17/3478* (2013.01);
(Continued)

(58) Field of Classification Search
CPC ........ A61B 2034/105; A61B 2034/107; A61B 34/00; A61B 34/10; A61B 5/103;
(Continued)

(56) References Cited

U.S. PATENT DOCUMENTS

2010/0317961 A1* 12/2010 Jenkins ................. A61B 5/055
                                                    600/411
2011/0236868 A1*  9/2011 Bronstein ............. G09B 23/30
                                                    434/267
(Continued)

FOREIGN PATENT DOCUMENTS

WO       2015023787 A1    2/2015

OTHER PUBLICATIONS

International Search Report and Written Opinion dated Mar. 18, 2019, for corresponding International Application No. PCT/US2018/063601, International Filing Date: Dec. 3, 2018 consisting of 11 pages.

*Primary Examiner* — William A Beutel
(74) *Attorney, Agent, or Firm* — Christopher & Weisberg, P.A.

(57) ABSTRACT

A method for enhancing a surgical procedure includes providing a three-dimensional model of a patient's organ of a patient based on pre-operative image data of the patient's organ; identifying positional data corresponding to a first position of at least one target treatment anatomy of the patient relative to a second position of an ancillary target anatomy of the patient based on an analysis of the three-dimensional model of the patient's organ of the patient; selecting a puncture location based on the identified positional data; and displaying, by an augmented reality device, a virtual organ object via an augmented reality display system overlaying a real-world environment, the virtual organ object corresponding to the three-dimensional model and visually indicating the selected puncture location.

14 Claims, 16 Drawing Sheets

(51) Int. Cl.

| | | |
|---|---|---|
| *A61B 5/044* | (2006.01) | |
| *A61B 17/00* | (2006.01) | |
| *A61B 90/00* | (2016.01) | |
| *A61M 25/01* | (2006.01) | |
| *A61B 90/50* | (2016.01) | |
| *A61M 25/00* | (2006.01) | |
| *A61B 34/20* | (2016.01) | |

(52) U.S. Cl.
CPC ............. *A61B 2017/00243* (2013.01); *A61B 2017/00292* (2013.01); *A61B 2017/00632* (2013.01); *A61B 2034/105* (2016.02); *A61B 2034/107* (2016.02); *A61B 2034/2065* (2016.02); *A61B 2090/367* (2016.02); *A61B 2090/374* (2016.02); *A61B 2090/378* (2016.02); *A61B 2090/3762* (2016.02); *A61B 2090/502* (2016.02); *A61M 2025/0089* (2013.01); *A61M 2025/0166* (2013.01)

(58) Field of Classification Search
CPC .. A61B 2018/00279; A61B 2018/0038; A61B 2018/00357; A61B 2018/00386; A61B 2017/00252; A61B 2017/22095; A61B 2017/22069; A61B 2017/00243; A61B 2017/3488; A61B 2017/3411; A61B 2017/3405; A61B 2018/00351; A61B 2017/00247; A61B 17/3403; A61B 34/20; A61B 17/3478; A61B 2034/2051; A61M 5/427

See application file for complete search history.

(56) References Cited

U.S. PATENT DOCUMENTS

| | | | |
|---|---|---|---|
| 2013/0150710 A1 | 6/2013 | Zentgraf et al. | |
| 2014/0187949 A1* | 7/2014 | Zhao | A61B 8/12 600/443 |
| 2016/0249989 A1* | 9/2016 | Devam | A61B 5/024 345/633 |
| 2016/0354057 A1* | 12/2016 | Hansen | A61B 8/0841 |
| 2017/0071479 A1* | 3/2017 | Kano | A61B 5/02007 |
| 2017/0215969 A1* | 8/2017 | Zhai | A61B 90/00 |
| 2018/0263688 A1* | 9/2018 | Barrish | A61M 25/00 |

* cited by examiner

AUGMENTED REALITY SOLUTION TO OPTIMIZE THE DIRECTIONAL APPROACH AND THERAPY DELIVERY OF INTERVENTIONAL CARDIOLOGY TOOLS

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for an augmented reality solution to optimize the directional approach and therapy delivery of interventional cardiology tools.

BACKGROUND

Many cardiac procedures are commonly performed in the left atrium of the heart, which is not easily accessible. In order to treat the left atrium, a device may enter the patient's circulatory system via the patient's femoral vein. The device then may be advanced through the femoral vein to the right atrium of the heart. Once in the right atrium, a transseptal puncture is typically created in the transseptal wall to gain access to the left side of the heart and associated vasculature.

Although transseptal puncture is commonly performed, life-threatening complications such as pericardial tamponade, aortic perforation, and systemic embolization may occur. Many of these occurrences are the result of unintentional puncturing of the atrial walls. For example, the beating of the heart, slipperiness of the myocardium, and irregularities in the thickness of the septum can contribute to the difficulty in steering a puncturing device, a catheter, or other devices and accurately puncturing the septum without causing injury.

Furthermore, the location of the septal puncture may significantly impact procedural complexity when conducting treatment procedures, such as, for example, cryoablation, pulmonary vein occlusion, left atrial appendage (LAA) closure, transcatheter mitral valve implantation (TMVI), transaortic valve implantation (TAVI), and the like. Due to the extreme manipulations required to attempt concentric positioning of a catheter balloon to one or more pulmonary veins, particularly the right inferior pulmonary vein (RIPV), catheter mechanical robustness has been shown to suffer, resulting in kinking of the guide wire lumen and may also result in leaking of the inner balloon bond. Such failures to achieve an optimal puncture location may negatively impact the ability of physicians to effectively steer such intracardiac medical devices and therefore may negatively impact patient safety and the procedure's efficacy.

In order to locate the precise area of the septal wall to be punctured, the physician may use one or more medical known imaging techniques, such as, for example fluoroscopy, endoscopy, or ultrasound visualization to identify the various anatomical boundaries that form the septum. However, existing techniques for locating an optimal puncture site in the septum wall have drawbacks.

For example, localization of a tip of a puncturing needle can be detected by the surgeon using various anatomical landmarks around the septum. In particular, the septum is comparatively thicker than the fossa ovalis in healthy patients providing an imprecise but potentially important physiological marker. However, in patients with atrial abnormalities, for example a dilated atrium, or as a result of previous surgeries, the traditional markers such as the fossa ovalis may change, making localization difficult and increasing the risk of harm to the patient.

Angiographic techniques have been devised to assist with locating puncture sites. For example, transesophageal and transthoracic echocardiography, intravascular ultrasound, and intracardiac echocardiography have all been employed as a means of determining the optimal transseptal puncture site. Transthoracic ultrasound, however, may not be capable of accurately locating the thin wall of the fossa ovalis and presents difficulties in maintaining both patient comfort and sterility, thus often resulting in an increased cost for a given procedure. Transesophageal echocardiography also presents several disadvantages in some cases, such as limited communication with the patient (resulting from sedation), a risk of esophageal bleeding, longer procedure times, additional cost, and inaccurate identification of the fossa ovalis. In addition, intracardial echocardiography is highly expensive and greatly increases the overall time of the procedure. Also, fluoroscopy imaging techniques require the use of x-rays that are known to be harmful to patients and necessitate physicians wearing heavy lead suits, which can inhibit the physician physically during the procedure, and, over time, may result in ergonomic complications for the physician.

Another problem with existing medical imaging techniques is that they typically involve conventional monitors (e.g., desktop monitors). In other words, during the procedure, the physician is required to look up from the operating table in order to view the images on the monitors. Doing so also requires the physician to look away from the patient and may result in inaccuracies in the procedure due to the physician constantly changing his/her field of view and focus. Some physicians may elect to forego the use of conventional monitors, or may not view the information on the monitors as frequently as they would prefer in order to avoid looking constantly looking away from the patient during the procedure.

Augmented reality devices blend computer-generated information with the user's view of the physical world, i.e., the real world. Stated another way, augmented reality devices augment computer-displayed information to the user's view of the real-world environment in order to enhance situational awareness of the user within the physical world with the computer-displayed information. However, existing augmented reality devices are rather limited in their use and have been primarily limited to personal use, rather than for medical imaging and procedures.

Accordingly, in light of the above limitations, it would be desirable to provide systems, devices, and methods for enhancing cardiac procedure efficacy and safety by using augmented reality devices to improve medical imaging, pre-operative planning, and intra-operative feedback techniques.

SUMMARY

The present invention advantageously provides a method and system for enhancing a surgical procedure. In particular, one aspect of the present invention includes provides a three-dimensional model of a heart of a patient based on image data of the heart of the patient. Positional data is identified corresponding to a first position of at least one target treatment anatomy of the patient relative to a second position of an ancillary target anatomy of the patient based on an analysis of the three-dimensional model of the heart of the patient. A puncture location is selected based on the identified positional data of the at least one target treatment anatomy of the patient relative to the second position of an ancillary target anatomy of the patient. An augmented reality device with an augmented reality display system displays a virtual organ object via the augmented reality display system overlaying a real-world environment, the virtual organ object corresponding to the three-dimensional model of the heart of the patient and visually indicating the selected puncture location. Each of the virtual organ object and at least a portion of the real-world environment are simultaneously viewable by a user of the augmented reality device via the augmented reality display system.

In this aspect, embodiments of the present invention include the real-world environment and the virtual organ object being simultaneously viewable within a single field of view of the user via the augmented reality display system. The positional data is associated with a computer-generated trajectory of a medical device from the ancillary target anatomy to the at least one target treatment anatomy; and the medical device includes one of a catheter and a left atrial appendage closure. The method may further include identifying a first candidate puncture location and a second candidate puncture location; determining a first trajectory from the first candidate puncture location to the at least one target treatment anatomy and a second trajectory from the second candidate puncture location to the at least one target treatment anatomy; selecting the puncture location based on a comparison of at least a first value associated with the first trajectory and at least a second value associated with the second trajectory; and visually indicating a one of the first trajectory and the second trajectory associated with the selected puncture location together with the visual indication of the selected puncture location on the virtual organ object being displayed in the displaying step. In addition, the at least a first value of the first trajectory and the at least a second value of the second trajectory being compared include at least one of an angle and a distance associated with the first trajectory and the second trajectory respectively. The visual indication of the one of the first trajectory and the second trajectory associated with the selected puncture location includes a line following a path of the one of the first trajectory and the second trajectory. Further, the user is a medical practitioner; the real-world environment is a surgical room for operating on the patient; and the virtual organ object is displayed during a surgical procedure within the surgical room. The image data includes pre-operative image data of the heart of the patient, the pre-operative image data associated with at least one of an MRI, an x-ray, an ultrasound, a fluoroscopy, an electrocardiogram, electro-anatomical mapping, and a CT scan of the heart of the patient. The method further includes tracking in real-time a movement of the heart of the patient during a surgery; and attaching the virtual organ object being displayed via the augmented reality display system with the tracked movement of the heart during the surgery. In addition, the method provides for tracking in real-time an intracardiac movement of a medical device within the heart of the patient during a surgery; and displaying a visual indication of the tracked intracardiac movement of the medical device on the virtual organ object being displayed during the surgery via the augmented reality display system. The visual indication of the tracked intracardiac movement of the medical device is simultaneously viewable via the augmented reality display system with the visual indication of the selected puncture location. A cross-sectional view of the heart of the patient is determined in order to display the virtual organ object via the augmented reality display system. A user-selection of a surgical procedure to be performed on the heart of the patient is received and the cross-sectional view of the heart of the patient to display via the augmented reality display system is determined based on the user-selection of the surgical procedure. The ancillary target anatomy is a fossa ovalis and the at least one target treatment anatomy is one of a pulmonary vein and a left atrial appendage. Thus, selecting the puncture location may further include selecting the puncture location based on a computer-generated trajectory from a location on the fossa ovalis to the one of the pulmonary vein and the left atrial appendage, and the visual indication of the selected puncture location being displayed via the augmented reality display system includes a visual indication of the computer-generated trajectory.

In another aspect of the present invention, an augmented reality system is provided with an augmented reality display system configured to be worn on a head of a user proximate the user's eyes; and processing circuitry in communication with the augmented reality display system. The processing circuitry is configured to provide a three-dimensional model of a heart of a patient based on image data of the heart of the patient; identify positional data corresponding to a first position of at least one target treatment anatomy of the patient relative to a second position of an ancillary target anatomy of the patient based on an analysis of the three-dimensional model of the heart of the patient; select a puncture location based on the identified positional data of the at least one target treatment anatomy of the patient relative to the second position of an ancillary target anatomy of the patient; and display, by an augmented reality device with an augmented reality display system, a virtual organ object via the augmented reality display system overlaying a real-world environment.

According to yet another aspect of the present invention, a method of enhancing a surgical procedure includes providing a three-dimensional model of an organ of a patient based on image data of the organ of the patient; and identifying positional data corresponding to a first position of at least one target treatment anatomy of the patient relative to a second position of an ancillary target anatomy of the patient based on an analysis of the three-dimensional model of the organ of the patient. The method further includes selecting a puncture location based on the identified positional data of the at least one target treatment anatomy of the patient relative to the second position of an ancillary target anatomy of the patient. An augmented reality device with an augmented reality display system displays a virtual organ object via the augmented reality display system overlaying a real-world environment. The virtual organ object corresponds to the three-dimensional model of the organ of the patient and visually indicates the selected puncture location. Each of the virtual organ object and at least a portion of the real-world environment are simultaneously viewable by a user of the augmented reality display system via the augmented reality display system.

Features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure describes systems, devices, and methods for enhancing cardiac procedure efficacy and safety by using augmented reality devices to improve medical imaging, pre-operative planning, and intra-operative feedback techniques. In addition, embodiments of the present disclosure are described with reference to one or more medical procedures; however, the present disclosure is not intended to be limited to any one or more of the particular medical procedures described herein as examples. In other words, it is contemplated that embodiments of the present disclosure may be associated with any medical procedure, whether or not expressly discussed herein, as embodiments of the present disclosure may be beneficial for a multitude of known, or future medical procedures.

Before describing in detail exemplary embodiments of the present disclosure, it should be noted that the terms "augmented reality" and "mixed reality" are used interchangeably and are intended to indicate devices, methods, and/or systems in which data, information, virtual images or objects, graphics, and the like, or other sensor, or computer-generated, actionable decision-making information are provided to the observer by a source, such as a display source (e.g., wearable devices or hologram projectors, etc.), within a real-world environment simultaneously observable by the observer. In some embodiments of the present disclosure described herein, "mixed reality" may further indicate devices, methods, and/or systems in which real-time data from one or more information sources is communicated, transmitted, streamed, and/or presented/rendered to the observer within the real-world environment. In yet other embodiments of the present disclosure, "mixed reality" and "augmented reality" may further indicate devices, methods, and/or systems in which the computer-generated information being presented/rendered to the observer as interacting with, or otherwise being tied to at least a portion of the real-world environment.

Figure 1:
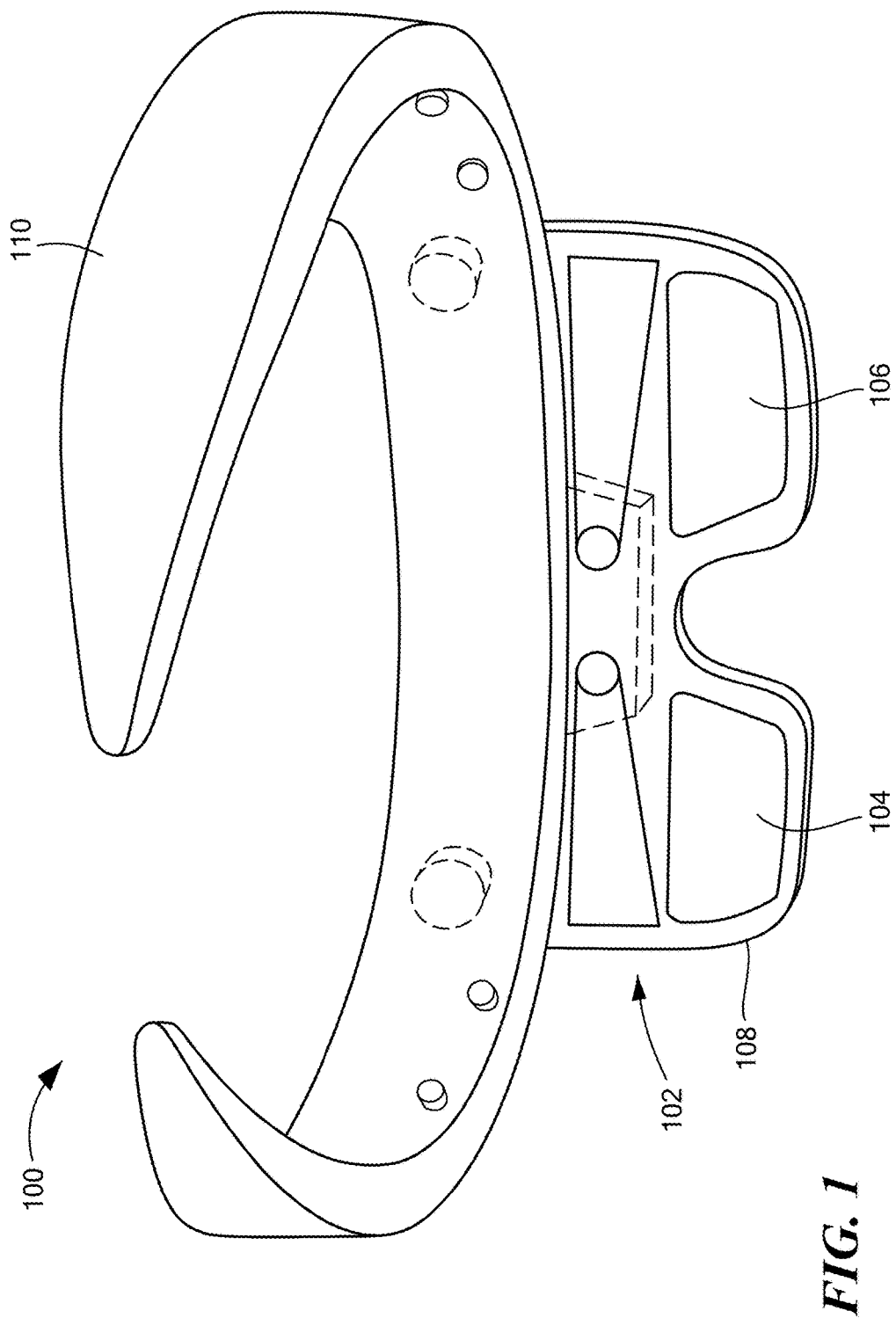
FIG. 1 illustrates a rear perspective view an exemplary augmented reality device in accordance with the principles of the present disclosure.
Figure 3:
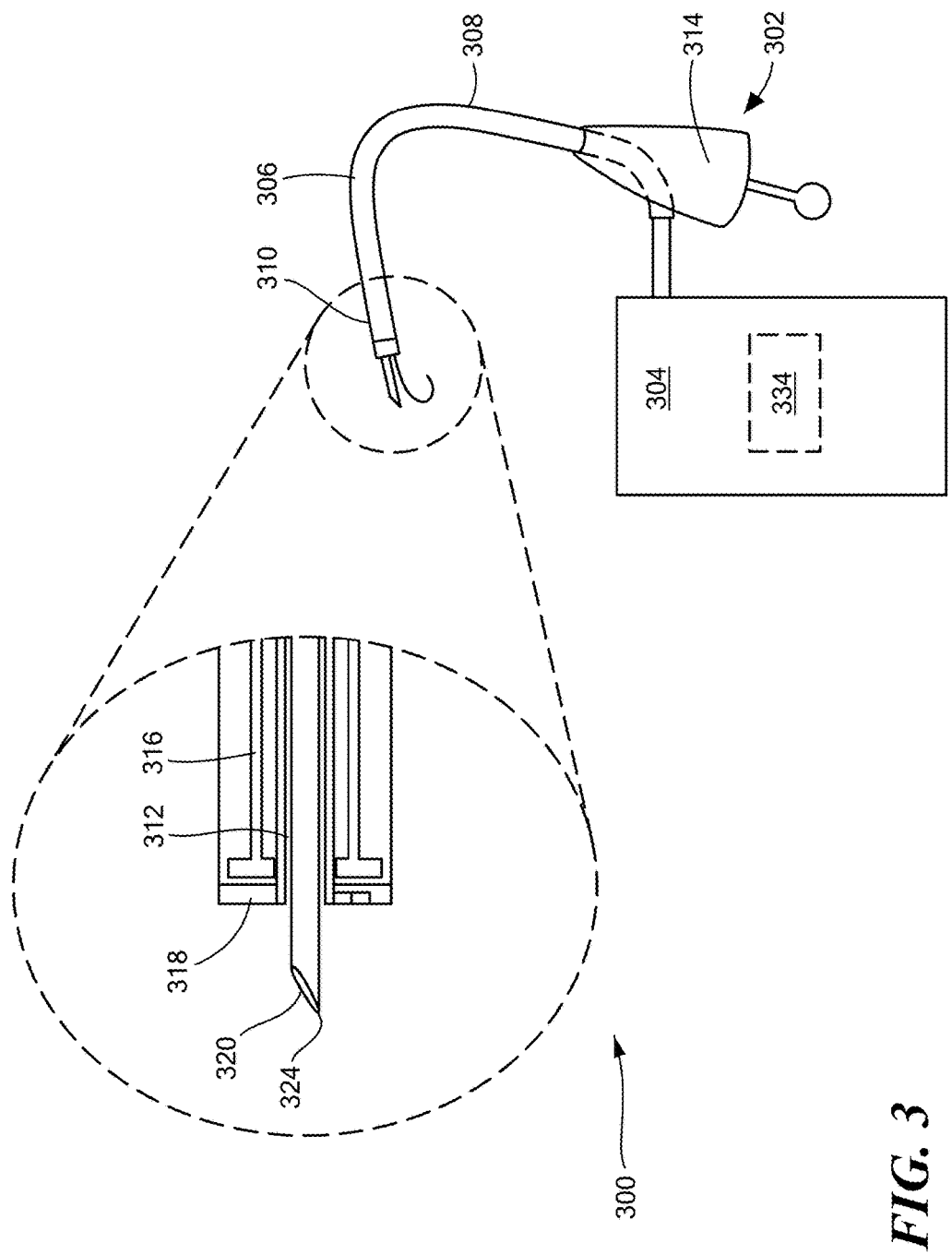
FIG. 3 illustrates an exemplary system for tissue puncturing in accordance with the present disclosure.
Figure 4:
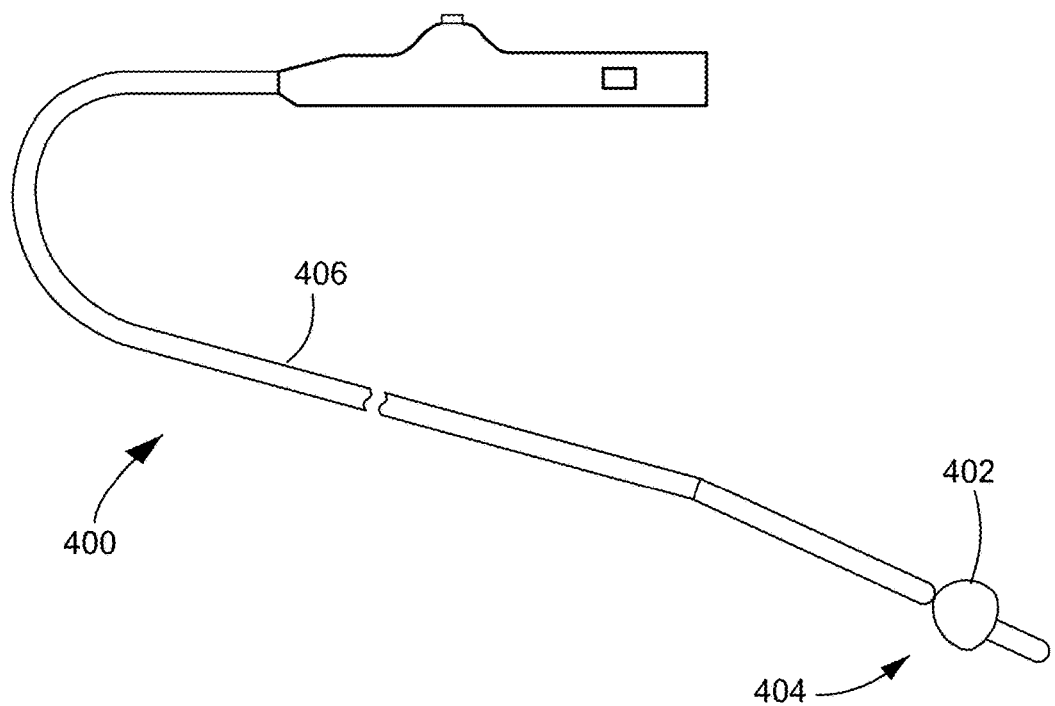
FIG. 4 illustrates an exemplary medical device.

Referring now to the drawing figures in which like reference designations refer to like elements, an embodiment of an augmented reality device in accordance with principles of the present invention is shown in FIG. 1 and generally designated as "100." FIGS. 3 and 4 show an embodiment of a tissue puncturing system 300 and a treatment device 400, respectively, in communication with the augmented reality device 100.

The following description will begin with an introduction of the various exemplary components of the augmented reality device 100, and the puncturing system 300 and treatment device 400, followed by a description of an exemplary method of using and/or implementing the devices and systems 100, 300, 400 in accordance with principles of the present disclosure.

Augmented Reality Device

The exemplary augmented reality device 100 is shown in FIG. 1 in the form of eyeglasses 102. The eyeglasses 102 include a pair of lenses 104, 106 and a frame 108 with a head support member 110 extending therefrom.

The head support member 110 is configured to support the augmented reality device 100 on a head of the wearer/user. The exemplary head support member 110 is shown in the form of a head band; however, alternative embodiments may be in the form of, for example, a pair of side arms configured to rest of the user's ears, as with traditional eyeglasses. The head support member 110, or another portion of the device 100, may be adapted as an augmented reality device housing, for housing the augmented reality device electrical and/or optical components, such as, for example, processing circuitry, sensors, cameras, network interfaces, and like, as will be described in more detail below with reference to the block diagram of FIG. 2.

The frame 108 and the head support member 110 can be formed of a solid rigid or semi-rigid polymer, plastic, and/or metal structure, or can be formed as a hollow structure of similar material to allow for wiring and interconnection of internal electrical components throughout the eyeglasses 102.

The lenses 104, 106 can be sufficiently transparent to allow the user to see through the lenses 104, 106 as is traditionally provided for non-computing eyeglasses. Stated another way, the lenses 104, 106 may be considered see-through lenses 104, 106. In some embodiments, the lenses 104, 106 may be prescription lenses. In other embodiments, the lenses 104, 106 may be slightly tinted. Although, FIG. 1 shows two lenses 104, 106, it is understood that the device 100 may include one lens or more than two lenses 104, 106.

Figure 2:
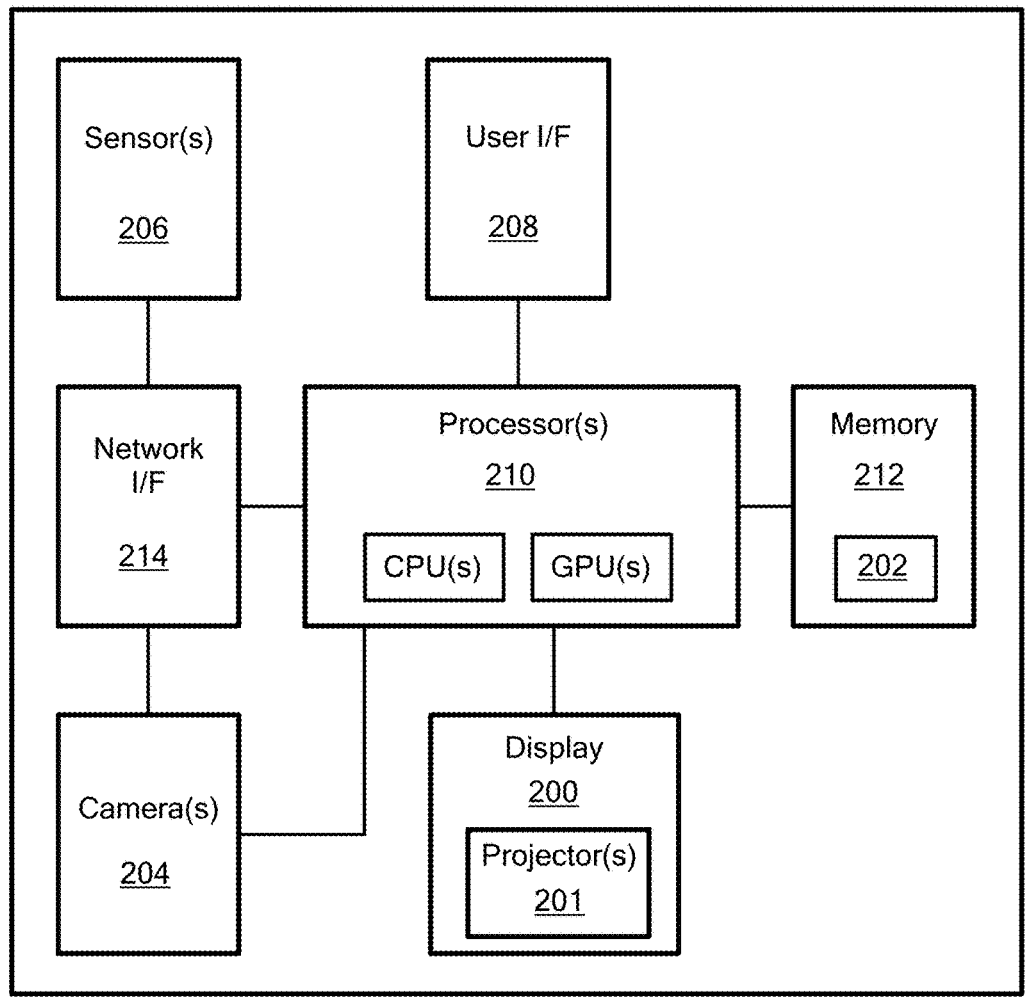
FIG. 2 illustrates a block diagram view of components of the augmented reality device of FIG. 1, in accordance with embodiments of the present disclosure.

Referring now primarily to FIG. 2, with brief reference to FIG. 1, the augmented reality device 100 can include computing components and optical components housed within the head support member 110, or otherwise supported by or included within the augmented reality device 100. The computing components and optical components may be coupled to the frame 108 and/or may be housed within the head support member 110. It is understood that any one of or a multitude of the computing and optical components may be provided on other parts of the eyeglasses 102 or can be remotely positioned, being in wireless or wired communication via a communication link with the eyeglasses 102.

FIG. 2 shows an example block diagram of exemplary components of the augmented reality device 100. The example device 100 may include an augmented reality display system 200, a cardiac augmented reality module 202, a camera 204, a sensor 206, a user input interface 208, a processor 210, memory 212, and a network interface 214.

The augmented reality display system 200 may, in one embodiment, be formed as a micro display and may be disposed in close proximity to the user's eye when worn. The micro display may be disposed between the lenses 104, 106 and the user's eye. The micro display may be a transparent or a semi-transparent display, and can be a matrix display, such as a light emitting diode (LED) display, a liquid crystal display (LCD), and the like. It is understood that any suitable display may be used provided that it allows the eyeglass user to view images as virtual objects (e.g., holograms) augmenting the user's view of the physical/real-world environment viewable through the lenses 104, 106. A display driver may provide an interface between the processor 210 and the display system 200, driving the display system 200. The display system 200, in conjunction with the display driver (not shown), is configured to display a virtual organ object (e.g., 1100, 902) overlaid over the user's view of the real-world through the lenses 104, 106.

Various techniques for displaying virtual objects using head-mounted, or other non-wearable augmented reality devices are known and may be used with embodiments of the present invention. In one embodiment, the display system 200 may be in communication with the processor 210 and may include projectors 201 that project an image onto a surface, such as the micro display. The processor 210 may process image data (e.g., a three-dimensional model of a heart), which is then fed into the projectors 201 for projecting an image onto the micro display or other display surface. The projectors 201 may be configured to project an image onto an interior display surface of the micro display, such that the image is viewable by the user as overlaying the user's view of the real-world environment through the lenses 104, 106. The display system 200 may also act as a light-projection system and may include a reflective coating, which reflects light projected onto a reflective surface directly into the user's retina. Other types of augmented reality display system technologies may also be used with embodiments of the present invention. In one embodiment, the augmented reality device 100 used in embodiments of the present invention is a Microsoft Hololens, which uses waveguides to overlay holograms on the user's real-world view. In yet other embodiments, the augmented reality device 100 used in embodiments of the present invention may include other known augmented reality devices, preferably head-mounted augmented reality devices. The components that implement the display element of virtual objects by the augmented reality device 100 may be referred to herein collectively as an "augmented reality display system."

In some embodiments, the augmented reality display system 200 may be formed as a smart contact wearable directly onto a wearer's eye. In yet another embodiment, the augmented reality display system 200 may include non-wearable elements, such as non-wearable projectors using, for example, spatial computing, mirrors, light refractors, cameras, and the like to display information (e.g., digital data, virtual objects, etc.) within the real-world environment.

The cardiac augmented reality module 202 may be configured to facilitate overlaying a virtual cardiac image over a view of the real-world through the lenses 104, 106, in accordance with known augmented reality techniques for overlaying images over a real-world view. In a further embodiment, the cardiac augmented reality module 202 may be responsible for performing some or all of the process steps described herein below with reference to the flow chart depicted in FIG. 5.

The cardiac augmented reality module 202 can be implemented as an executable instruction set that is resident in and executed by the device 100. In one implementation, the cardiac augmented reality module 202 may be one or more programs that are stored on a computer or machine readable medium. In the exemplary implementation, the cardiac augmented reality module 202 is stored in the memory 212. The cardiac augmented reality module 202 may be a stand-alone software application or form a part of a software application that carries out additional tasks related to the augmented reality device 100. Also, while the cardiac augmented reality module 202 is implemented in software in accordance with an implementation of the present invention, such functionality could also be carried out via dedicated hardware or firmware, or some combination of hardware, firmware, and/or software.

The camera 204 includes a camera lens and may be configured to capture still images as well as video. In one embodiment, the augmented reality device 100 may include more than one camera 204. The camera lens may face forward (that is, away from the wearer's/user's face when the augmented reality device 100 is in use) to capture still images and video of at least a portion of a real world view as perceived by a user wearing the eyeglasses 102. The images captured by the camera 204 can be stored in the memory 212 for use in displaying the virtual organ object (e.g., 1100, 902) overlaid over a real-world view as perceived by the user through the lenses 104, 106. In other embodiments, the augmented reality device 100 may include more than one camera 204 to, for example, capture a wide field of view of the real world.

The sensor 206 may be disposed on and/or within the head support member 110 and be configured to sense or detect aspects of the real-world environment, such as, for example, an orientation of the user's head. The augmented reality device 100 may include more than one sensor 206. In one embodiment, the sensor 206 can be, for example, an accelerometer or proximity sensor, or other sensor known in the art. The sensor 206 can, for example, detect when the user has removed the eyeglasses 102 for powering down the device 100 or placing the device 100 in sleep mode during periods of non-use. In other embodiments, the augmented reality device 100 may include a plurality of sensors 206 to track, for example, user gaze and sense hand movements and gestures for use by the user input interface 208. Preferably, the augmented reality device 100 includes a multitude of sensors 206 in order to sense the physical world that the user is within, as well as, to detect the user himself/herself and, more specifically, his/her movements, gaze, head orientation, etc. Such sensors 206 may allow the augmented reality device 100 to combine real-world data with virtual image data in order to provide a more immersive and accurately augmented experience for the physician and/or to allow the virtual images to interact with aspects of the real-world.

The user input interface 208 is configured to allow the user to provide input to the augmented reality device 100, such as, for example, user selections, commands, and the like. In one embodiment, the user input interface 208 includes a finger-operable touch pad disposed on the head support member 110 that can detect at least one of a position, pressure, and a movement of a finger via apparatuses and methods well-known in the art, such as capacitive sensing, resistance sensing, and the like. For example, the user may tap the touch pad with his or her finger to initiate or deactivate software applications responsible for generating and displaying cardiac images as augmented reality images in accordance with techniques described herein. In another embodiment, the device 100 may include sensors 206 configured to sense the user's hand gestures as user input, in accordance with known methods and devices in the art of augmented reality devices. Other user input devices may be integrated into the augmented reality device 100, such as a microphone for voice recognition commands, a physical or virtual keyboard, movement sensors, gaze tracking cameras, pointing devices, and/or other user input methods and devices (not shown).

The processor 210 can be, for example, a central processing unit (CPU), a controller, a microcontroller, or a microprocessor, including a "general purpose" microprocessor or a special purpose microprocessor. The processor 210 executes code stored in memory 212 and/or non-volatile storage in order to carry out operation of the augmented reality device 100. The processor 210 can provide the processing capability to execute an operating system, run various applications, and provide processing for one or more of the techniques, functions, and/or methods described herein. The terms "processor" and "processing circuitry," as used herein, are intended broadly to encompass a single processor or multiple processors and other processing circuitry providing the processing for one or more of the techniques, functions, and/or methods described herein. The augmented reality device 100 preferably includes one or more CPUs, as well as one or more graphics processing units (GPUs) in order to process large amounts of image data.

The memory 212 associated with the augmented reality device 100 can be, for example, one or more of a buffer, register, flash memory, or random access memory (RAM). The memory 212 may also include non-volatile storage. The non-volatile storage can represent any suitable storage medium, such as a hard disk drive or non-volatile memory, such as flash memory, and the like.

The network interface 214 can include one or more network interface cards (NIC) that can provide the capability for the augmented reality device 100 to network with, for example, a personal area network (PAN), such as a Bluetooth® network, a local area network (LAN), such as a Wi-Fi network, or a wide area network (WAN), such as the Internet or a cellular mobile communications network, for example. The network interface 214 may facilitate communication over one or more wired and/or wireless network connections. The network interface 214 may facilitate communications between the augmented reality device 100, the tissue puncturing system 300, the treatment device 400, and other devices and systems, such as a navigation system and a mapping system. For example, pre-operative image data, such as a computed tomography (CT) scan of a patient, may be transmitted wirelessly to the augmented reality device 100 via the network interface 214 for generating a virtual organ object based on the CT scan.

Tissue Puncturing System

Referring now primarily to FIG. 3, a tissue puncturing system 300 is described for engaging and puncturing tissue, such as a septum. The system 300 may generally include a puncture device 302 for anchoring tissue and performing transseptal punctures and a control unit 304 for operating, monitoring, and regulating the operation of the puncture device 302.

In one embodiment, the device puncture 302 includes a flexible elongate body 306 having a proximal portion 308, a distal portion 310, and a lumen 312. The elongate body 306 may be, for example, a flexible catheter suitable for intravascular procedures. The elongate body 306 may define one or more secondary lumens disposed within, and the lumen 312 and/or secondary lumens may provide mechanical, electrical, and/or fluid communication between the proximal portion 308 of the elongate body 306 and the distal portion 310 of the elongate body 306. The lumen 312 (and optionally, secondary lumens) may be thermally insulated. Further, the lumen 312 may define a distal aperture 313 in the distal end of the puncture device 302. Thus, the lumen 312 may be open to the surrounding environment and may be sized and configured to allow one or more device components to pass therethrough and extend distally beyond the distal end of the elongate body 306.

The proximal end 308 of the elongate body 306 may be coupled to a handle 314, which may include various ports for electrical and fluid connectors, leads, junctions, or tubes, and may also include various control assemblies, such as switches or valves, as well as safety detection or shutdown components. For example, the handle 314 may include connectors that are matable directly or indirectly by way of one or more umbilicals to the control unit 304. Further, the handle 314 may also include an element such as a lever or knob for manipulating or deflecting at least a portion of the elongate body 306.

The puncture device 302 may further include a fluid flow path 316 disposed within, as shown in FIG. 3. For example, in one embodiment, the puncture device 302 may include a fluid flow path 316 that is in fluid communication with a source of coolant. Circulation of the coolant within the fluid flow path 316 may enable the puncture device 302 to cryoadhere to an area of tissue such as the septum, thereby anchoring the device to and stabilizing the septum in order to facilitate puncture. Further, if the puncture device 302 is used for cryoadhesion as well as puncture, the puncture device 302 may include a thermally transmissive region 318 in fluid communication with the fluid flow path 316. The thermally transmissive region 318 may surround or at least partially surround the distal aperture 313, thereby anchoring the puncture device 302 to the area of tissue while still allowing passage of one or more device components through the distal aperture 313.

The puncture device 302 may further include a puncturing element 320 movably disposed within the lumen 312 to create an opening in tissue engaged with the treatment device 400. The puncturing element 320 may be any sufficiently pointed component capable of puncturing tissue, such as a needle. In another example, the puncturing element 320 may be a guide wire. The puncturing element 320 may be insertable into the lumen 312 of the elongate body 306 and may be passable through the distal aperture 313 and extendable distally beyond the distal end of the elongate body 306. The puncturing element 320 may be removably or permanently coupled to the puncture device 302 at either the handle 314 or at any point along the elongate body 306. Further, the puncturing element 320 may be disposed within the puncture device 302 in an off-axis manner so as to allow the concurrent passage of a secondary device (or a guide wire) through the lumen 312. The puncturing element 320 may have a distal end 324 movable about the elongate body 306, and may include a number of different geometries or bevels (such as a point, conical reverse bevel or tangential back bevel) suitable to perform tissue puncture.

The system 10 may optionally further include one or more sensors (not shown) to monitor the operating parameters throughout the system, including for example, pressure, temperature, flow rates, volume, or the like in the control unit 304 and/or the puncture device 302, in addition to monitoring, recording or otherwise conveying measurements or conditions within the puncture device 302 or the ambient environment at the distal portion of the puncture device 302. The sensor(s) may be in communication with the control unit 304 for initiating or triggering one or more alerts or coolant delivery modifications during operation of the puncture device 302. One or more valves, controllers, or the like may be in communication with the sensor(s) to provide for the controlled dispersion or circulation of fluid through the lumens/fluid paths of the puncture device 302. Such valves, controllers, or the like may be located in a portion of the puncture device 302 and/or in the control unit 304. In one embodiment, the puncture device 302 includes one or more pressure sensors coupled to the elongate body distal portion 310 to facilitate positioning of the puncture device 302 in contact with, for example, the septum during the puncture procedure.

The control unit 304 may further include a user interface 334, which may include an LCD touch screen or other display device that displays status and data of the system 300, as well as accepting user data and control inputs. Various discrete indicators, controls, and displays may also be included which indicate the status of one or more control unit 304 parameters and allow inputs for manual operation of the system 300. The user interface 334 may include one or more visual displays and/or one or more electrical or mechanical input components. The control unit 304 may also include one or more controllers, processors, and/or software modules containing instructions or algorithms to provide for the automated operation and performance of the features, sequences, or procedures described herein. In one embodiment, the user interface 334 associated with the control unit 304 may be provided in the augmented reality device 100. Accordingly, control inputs to and feedback from the control unit 304 and/or the puncture device 302 may be through the augmented reality device 100. For example, feedback data may be displayable via the display system 200 of the device and user inputs may be provided by the user of the device 100 by, for example, voice commands.

If the puncture device 302 is used for cryoadhesion as well as puncture, the control unit 304 may be operated to maintain a temperature of the thermally-transmissive region 318 low enough to achieve effective cryoadhesion to a tissue region, while preventing unwanted permanent tissue injury associated with ablative or necrotic freezing. For example, the target temperature range may be between approximately 0° C. and approximately negative 30° C. (−30° C.).

After puncturing the tissue with the puncturing element 320, the puncture device 302 may be removed from the patient's body and replaced with one or more post-puncture treatment devices or other secondary devices, such as, for example, catheters, dilators, sheaths, valves, prostheses, and the like, or other devices for imaging, mapping, and/or diagnosis.

Treatment Device System

The following is a description of an exemplary post-puncture treatment device 400 that may be used in embodiments of the present disclosure. Referring now primarily to FIG. 4, with reference also to close-up views in FIGS. 8a-b, the exemplary treatment device 400 is shown and may include one or more connections to selectively couple the treatment device 400 to the control unit 304 for monitoring and/or controlling one or more features of the treatment device 400.

The treatment device 400 may include one or more treatment regions for energetic or other therapeutic interaction between the treatment device 400 and a treatment site, such as, for example, a pulmonary vein or an LAA. In one embodiment, the treatment device 400 is a catheter. The treatment regions may deliver, for example, radiofrequency energy, electroporation energy, cryogenic therapy, or the like to a tissue area in proximity to the treatment region(s) for the treatment, evaluation, or other interaction with the tissue. For example, the treatment device 400 may include a treatment region 402 having a thermal treatment element, such as an expandable membrane or balloon and/or one or more electrodes or other thermally-transmissive components, at least partially disposed on an elongate body 406. In a particular example, the treatment region 402 may include a first expandable/inflatable element or balloon 800 (see FIGS. 8*a-b*) coupled to a distal portion 404 of the elongate body 406 of the treatment device 400. In addition, the expandable element 800 may have any of a myriad of shapes, and may further include one or more material layers providing for puncture resistance, radiopacity, or the like. The expandable element 800 may be in communication with the fluid injection and exhaust lumens of the treatment device 400, which may be constructed and may operate similarly to the lumens described above with reference to the fluid flow path 316 in the puncture device 302 shown in FIG. 3. In other words, the treatment device 400 may also be configured to transport fluids, such as coolant, to the expandable element 800 to, for example, cryoablate tissue corresponding to a pulmonary vein opening. In addition, the fluid injection and/or exhaust lumens may be slidably positionable and movable within the expandable element 800 to direct coolant or fluid dispersion towards a desired portion of the expandable element 800, such as a distal or a proximal portion. However, it will be understood that any type, number, or configuration of treatment region 402 may be used.

Figure 5:
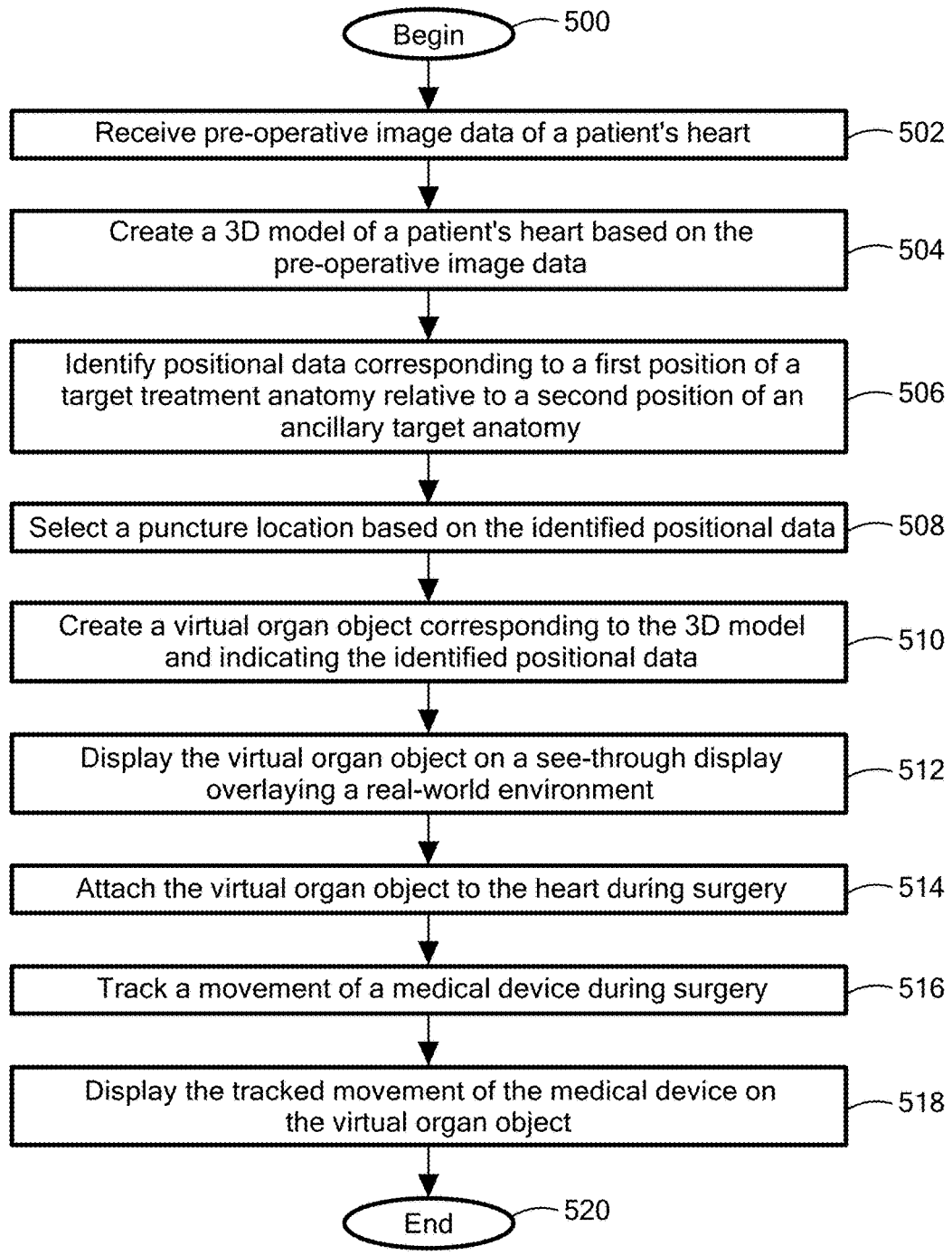
FIG. 5 illustrates a flow chart of an exemplary method of using the augmented reality device of FIG. 1, the tissue puncturing system of FIG. 3, and the medical device of FIG. 4, in accordance with embodiments of the present disclosure.

Method of Providing an Augmented Reality Solution to Optimize the Directional Approach and Therapy Delivery of Interventional Cardiology Tools Referring now to the flow chart shown in FIG. 5, with reference also to FIGS. 6-15, an exemplary method of using the augmented reality device 100 of FIGS. 1 and 2, the tissue puncturing system 300 of FIG. 3, and the treatment device 400 of FIG. 4, in accordance with principles of the present disclosure is described.

Although FIG. 5 shows a specific order of executing functional logic blocks, the order of executing the blocks may be changed relative to the order shown. Also, two or more blocks shown in succession may be executed concurrently or with partial concurrence. Certain blocks may also be omitted for the sake of brevity. And some blocks are merely exemplary steps in an exemplary implementation, but are not required in order to be in accordance with the present invention.

The method may begin at step 500 and immediately proceed to step 502, where pre-operative image data is received. The pre-operative image data may be imaging data of a patient's organ. In one embodiment, the organ is the patient's heart. In embodiments, the pre-operative image data of the patient's heart may include image data associated with, for example, a magnetic resonance imaging (MRI), an x-ray, an ultrasound, a fluoroscopy, an electrocardiogram, and/or a computed tomography (CT) scan of the patient's heart. Of note, such image data is typically obtained prior to a surgical procedure in order to determine if the surgical procedure is warranted. Techniques and devices for providing pre-operative image data are well-known in the art and therefore will not be described in great detail herein.

In step 504, a three-dimensional (3D) model of the patient's heart 600 (see FIG. 6) may be created based on the pre-operative image data. Some embodiments may use a single pre-operative imaging technique (e.g., a CT scan) to create the 3D model, and other embodiments may use data combined from a plurality of techniques (e.g., an ultrasound and an electrocardiogram) to create the 3D model. In one embodiment, the augmented reality device 100, or more specifically the one or more processors 210, may create the 3D model based on received pre-operative image data. In another embodiment, a separate computing device may create the 3D model and may communicate or otherwise provide the 3D model to the augmented reality device 100. In one embodiment, the 3D model may be created by, for example, a software application that may apply various 3D modeling techniques on the pre-operative image data. The 3D modeling techniques may include, for example, segmenting the pre-operative image data to identify the area(s) of interest, followed by mesh refinement of the area(s) of interest, and further 3D refining techniques, such as repairing the mesh, correcting errors, smoothing surfaces, and the like. Applications and techniques for transforming medical imaging data into 3D models are known in the medical industry to, for example, 3D print replacement or model anatomical parts. These and other known applications and techniques for creating 3D models may be used in embodiments of the present invention to create a 3D model for use by the augmented reality device 100.

In a preferred embodiment, the 3D model should be a 3D model of the patient's heart 600 and should include a 3D model of the area(s) of interest, such as, an ancillary target anatomy, and at least one target treatment anatomy of the patient. The particular areas of interest may be the areas of the heart 600 relevant to the surgical procedure to be performed on the patient's heart 600. The ancillary target treatment anatomy may be considered an anatomical feature of the patient that supports treatment of the target treatment anatomy, but is not itself the target treatment anatomy, such as, a puncturing location to access the target treatment anatomy. The target treatment anatomy may be considered one or more anatomical features of the patient that are intended for treatment, such as, for example, an occlusion of the right inferior pulmonary vein 604, the right superior pulmonary vein 610, left inferior pulmonary vein 606, and/or the left superior pulmonary vein 608 (see FIG. 6).

Figure 6:
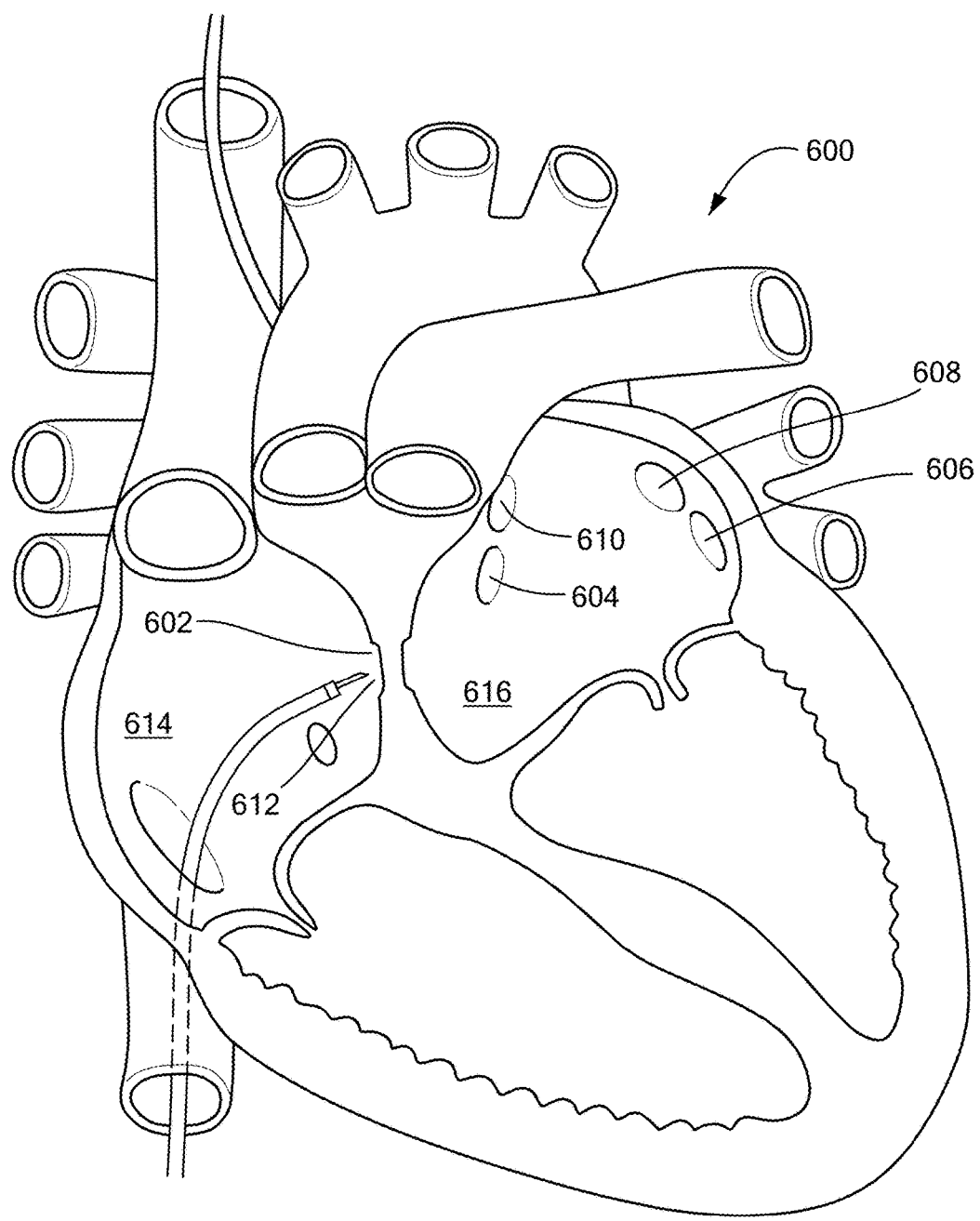
FIG. 6 illustrates a heart with a septum wall that is being prepared for puncturing by the tissue puncturing system of FIG. 3, in accordance with an embodiment of the present disclosure.
Figure 16:
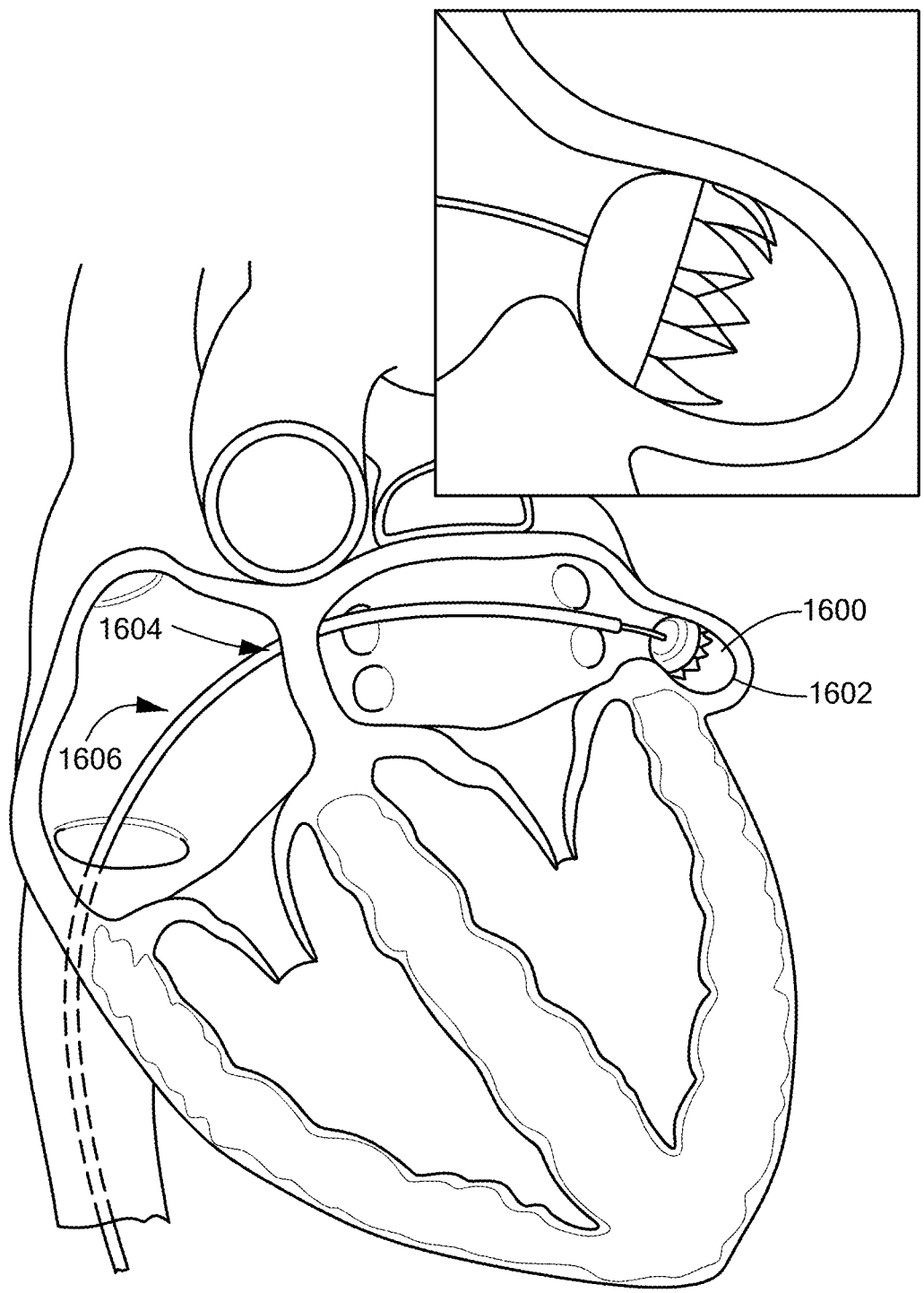
FIG. 16 illustrates an exemplary optimal septal puncture location and LAA closure device trajectory configured to properly seat the LAA closure device in accordance with an alternative embodiment of the present disclosure.

In one preferred embodiment, the ancillary target anatomy is a septum wall 602 for puncturing an access opening therein, and the target treatment anatomy may be one or more pulmonary veins 604, 606, 608, 610 (for pulmonary occlusion), or an LAA (for LAA closure) (see FIGS. 6 and 16, respectively). More specifically, the ancillary target anatomy may be a fossa ovalis 612, which is a depression in a right atrium 614 of the heart 600 at the septum wall 602 that is generally thinner than a remainder of the septum wall 602 and therefore may present an optimal puncture site to access a left atrium 616 of the patient.

In one embodiment, the 3D model includes a cross-sectional view of the heart 600 that shows the area(s) of interest, such as the cross-sectional views depicted in FIGS. 6 and 16. In one embodiment, a user may input (into the augmented reality device 100 or another computing system in communication with the augmented reality device 100) a selected cross-sectional view and/or surgical procedure prior to the creation of the 3D model. Accordingly, the 3D model may be created to include the selected cross-sectional view relevant for the selected surgical procedure. In another embodiment for systems dedicated to a particular type of surgical procedure, the selected cross-sectional view may be a default cross-sectional view. In further embodiments, the 3D model may include a plurality of cross-sectional views of the heart from which the surgeon/physician may select to view on the augmented reality device 100 on-the-fly during pre-operation planning as well as during the procedure itself.

In step 506, positional data may be identified corresponding to a first position of at least one target treatment anatomy of the patient relative to a second position of the ancillary target anatomy of the patient. The positional data may be based on a computer-analysis of data corresponding to the 3D model of the patient's heart 600 and may be based on the particular surgical procedure to be performed on the patient's heart 600.

Figure 7:
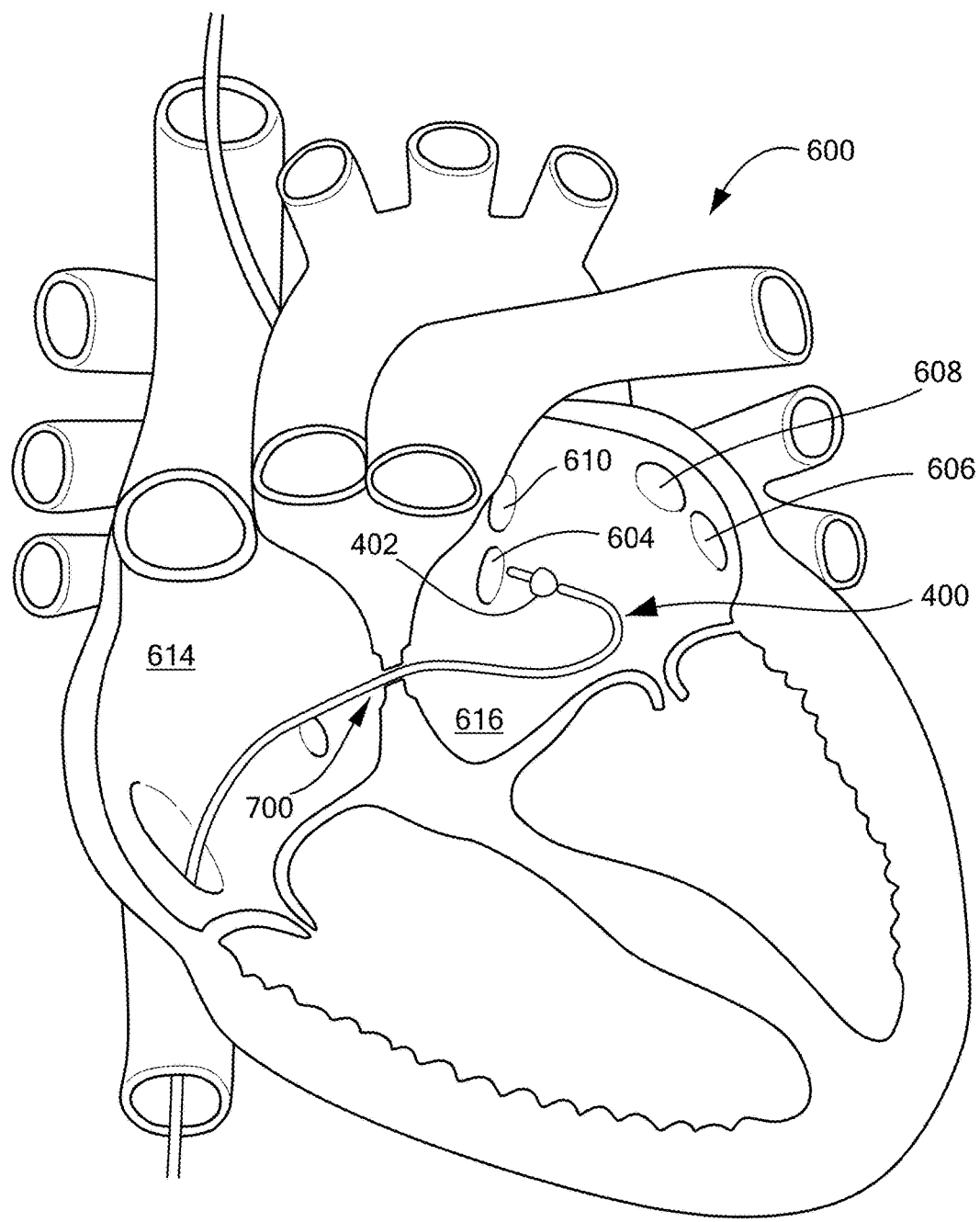
FIG. 7 illustrates the catheter of FIG. 4 being steered within the left atrium toward a pulmonary vein according to an embodiment of the present disclosure.

Referring now briefly to FIGS. 6-8, an exemplary surgical procedure will be described for enhancement by embodiments of the present disclosure. As discussed herein above in the Background section, some cardiac procedures are commonly performed in the left atrium 616 of the heart 600, which is not easily accessible. In order to treat anatomical areas within the left atrium 616, a device may enter the patient's circulatory system via the patient's femoral vein. The device then may be advanced through the femoral vein to the right atrium 614 of the heart 600. Once in the right atrium, a puncture is typically created in the septum wall 602 to gain access to the left side of the heart and associated vasculature, as illustrated in FIG. 7. More specifically, the fossa ovalis 612 at the septum wall 602 is typically punctured. With that said, the location of the puncture may significantly impact procedural complexity when conducting treatment procedures, such as, cryo-ablation, pulmonary vein occlusion, or left atrial appendage (LAA) closure.

Figure 8A:
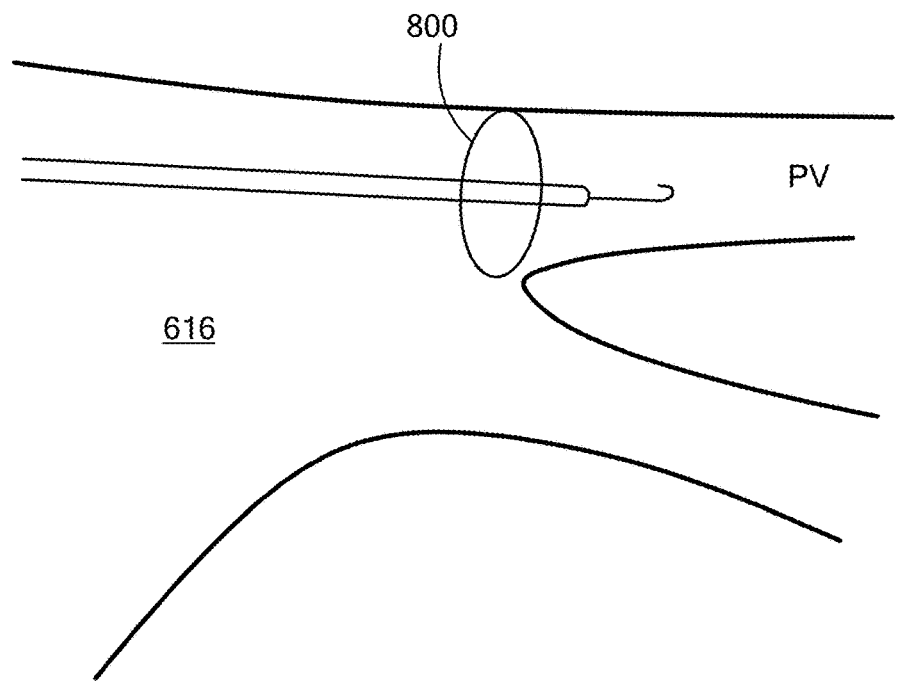
FIGS. 8a and 8b illustrate an incomplete occlusion of the pulmonary vein in FIG. 7 and a complete occlusion of the pulmonary vein in FIG. 7, respectively.
Figure 8B:
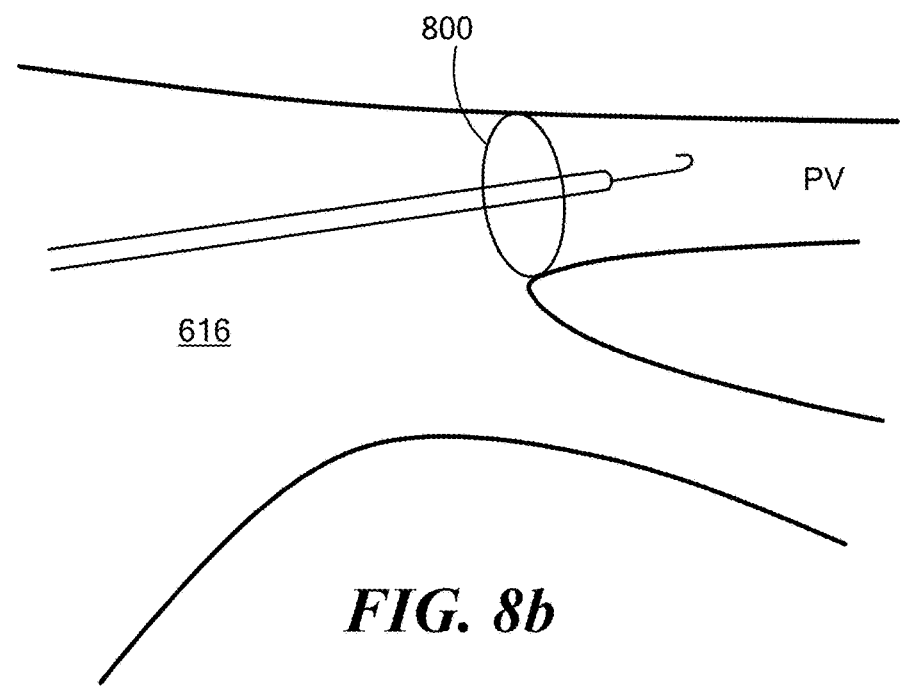

For example, cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like). Procedures such as pulmonary vein isolation (PVI) are commonly used to treat atrial fibrillation. This procedure generally involves the use of a cryogenic device, such as the treatment device 400, which is navigated toward the ostium of the pulmonary vein (PV) 604, 606, 608 and/or 610, as shown in FIG. 7. Ideally, the treatment device 400 should completely occlude the PV (that is, block the blood flow exiting the PV into the left atrium 614). Once in position, the treatment region 402 of the treatment device 400, for example, the expandable balloon 800 may be activated (e.g., fluid coolant delivered to the balloon 800) for a sufficient duration to create a desired lesion within myocardial tissue at the PV-LA junction, as shown in FIG. 8b. The fluid coolant of the cryo-balloon 800 enables the balloon 800 to create a circumferential lesion about an opening (ostium and/or antrum) of the PV 604, 606, 608 and/or 610 to disrupt aberrant electrical signals exiting the PV 604, 606, 608 and/or 610.

The success of this procedure depends largely on the quality of the lesion(s) created during the procedure and whether the cryo-balloon 800 has completely occluded the PV, as shown in FIG. 8b. Incomplete occlusion, as shown in FIG. 8a, allows blood to flow from the PV 604, 606, 608 and/or 610 being treated, past the cryo-balloon 800, and into the left atrium 616 of the heart 600. This flow of warm blood may prevent the cryo-balloon 800 from reaching temperatures low enough to create permanent lesions in the target tissue. The creation of reversible lesions may not be sufficient to achieve electrical isolation and, as a result, atrial fibrillation may be likely to reoccur. Accordingly, complete occlusion of the PV 604, 606, 608 and/or 610 is required for successful treatment of the target tissue area.

Against this backdrop, Applicant has discovered that the physician may experience more difficulty in approaching and treating the target PV 604, 606, 608 and/or 610 for certain septal puncture locations, as compared to other septal puncture locations. For example, it has been discovered that physicians may experience more difficulty in approaching and treating the right inferior pulmonary vein (RIPV) 604 if a septal puncture 700 is located close to the RIPV 604. In other words, more steering and manipulation of the treatment device 400 may be required in order to traverse a more acute angle between the RIPV and the septal puncture location 700, as compared to, for example, a puncture location that is farther from the RIPV. Specifically, Applicant has discovered that more uniform occlusion of the pulmonary veins 604, 606, 608 and/or 610 has been achieved when the septal puncture location 700 is anterior and superior away from the RIPV.

Figure 10C:
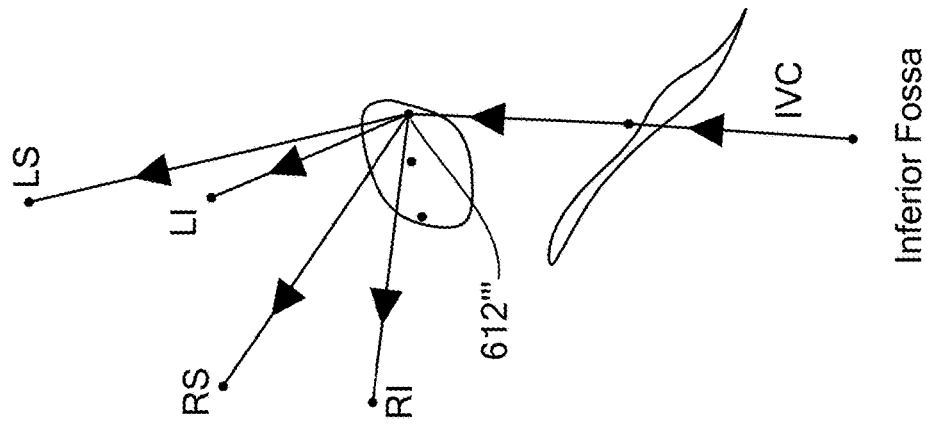
FIG. 10 illustrates angle and distance data to each pulmonary vein of a human subject based on the septal puncture location in accordance with embodiments of the present disclosure.
Figure 10B:
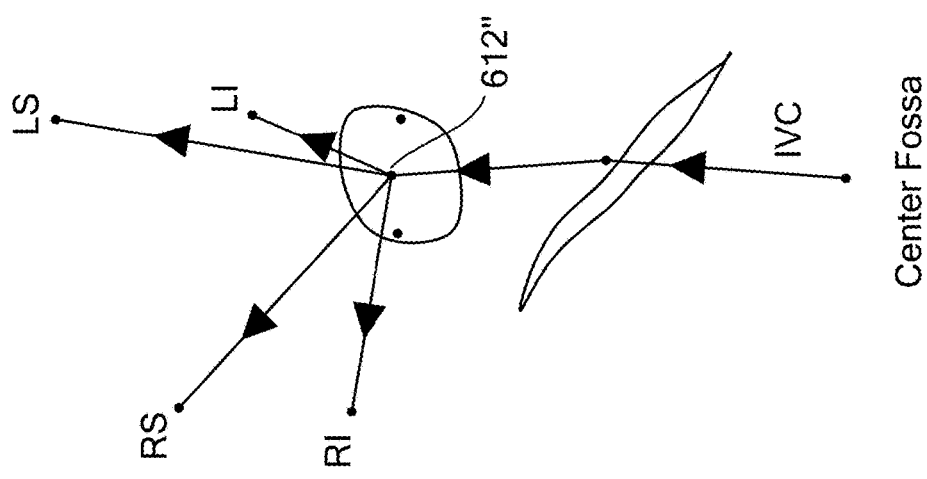
Figure 10A:
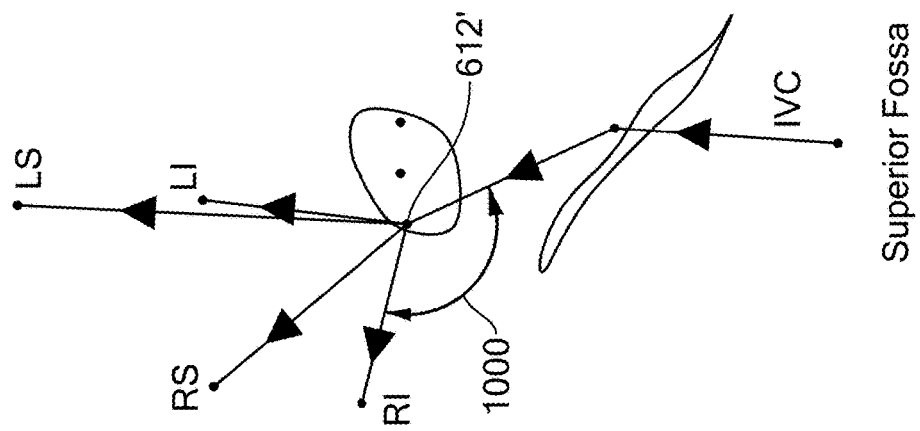

Referring now to FIG. 10, a chart is shown representing human anatomical data corresponding to an angle and a distance to each pulmonary vein 604, 606, 608 and/or 610 from a location of the septal puncture 700 at the fossa ovalis 612. A candidate puncture location at each of a superior fossa ovalis location 612', a center fossa ovalis location 612", and an inferior fossa ovalis location 612'" was identified and analyzed to determine an optimal puncture location and medical device trajectory. Tables of the data are shown herein below.

TABLE 1 shows the 3D Angle (degrees) from three different puncture locations at the fossa ovalis (FO) (superior 612', center 612", inferior 612'") to each of the PVs, as follows:

|  | Right Superior (RS) PV | Right Inferior (RI) PV | Left Superior (LS) PV | Left Inferior (LI) PV |
| --- | --- | --- | --- | --- |
| Superior FO | 138 +/− 9.4 | 122.5 +/− 12.5 | 152.2 +/− 15.7 | 140 +/− 22.9 |
| Center FO | 119.3 +/− 11.1 | 102.7 +/− 12.5 | 150.7 +/− 14.8 | 141.1 +/− 19.4 |
| Inferior FO | 108.7 +/− 5.7 | 97.3 +/− 13 | 154.3 +/− 10.9 | 143.2 +/− 16.8 |

TABLE 2 shows the distance (millimeters) from three different puncture locations at the fossa ovalis (superior 612', center 612", inferior 612'") to each of the PVs, as follows:

|  | Right Superior (RS) PV | Right Inferior (RI) PV | Left Superior (LS) PV | Left Inferior (LI) PV |
| --- | --- | --- | --- | --- |
| Superior Fossa | 36.1 +/− 6.8 | 31.9 +/− 6.3 | 59.6 +/− 2.4 | 54.5 +/− 2.1 |
| Center Fossa | 38.9 +/− 7.5 | 36.8 +/− 7.2 | 55.7 +/− 3.4 | 54 +/− 4 |
| Inferior Fossa | 45.7 +/− 5.9 | 44.6 +/− 8 | 57.4 +/− 2.7 | 52.5 +/− 3.4 |

As can be seen by the images in FIG. 10 and the angle and distance data shown in Tables 1 and 2, respectively, the shortest distances to the RS and RI PVs are the superior and center fossa ovalis locations 612' and 612". The more acute angles 1000 for the RS and RI PVs are at the inferior fossa ovalis location 612'''. Accordingly, it may be preferred to select the superior or center fossa ovalis location 612" or 612''' as the selected puncture location 700 in order to reduce the complexity of the steering for an occlusion of the RIPV 604. In one embodiment, a computing device (e.g., device 100) may select a puncture location having at least one of a larger angle value and/or a shorter distance value as the selected puncture location 700. In other embodiments, the physician may provide a user input to the computing device in order to select or change the selected puncture location 700.

Figure 11:
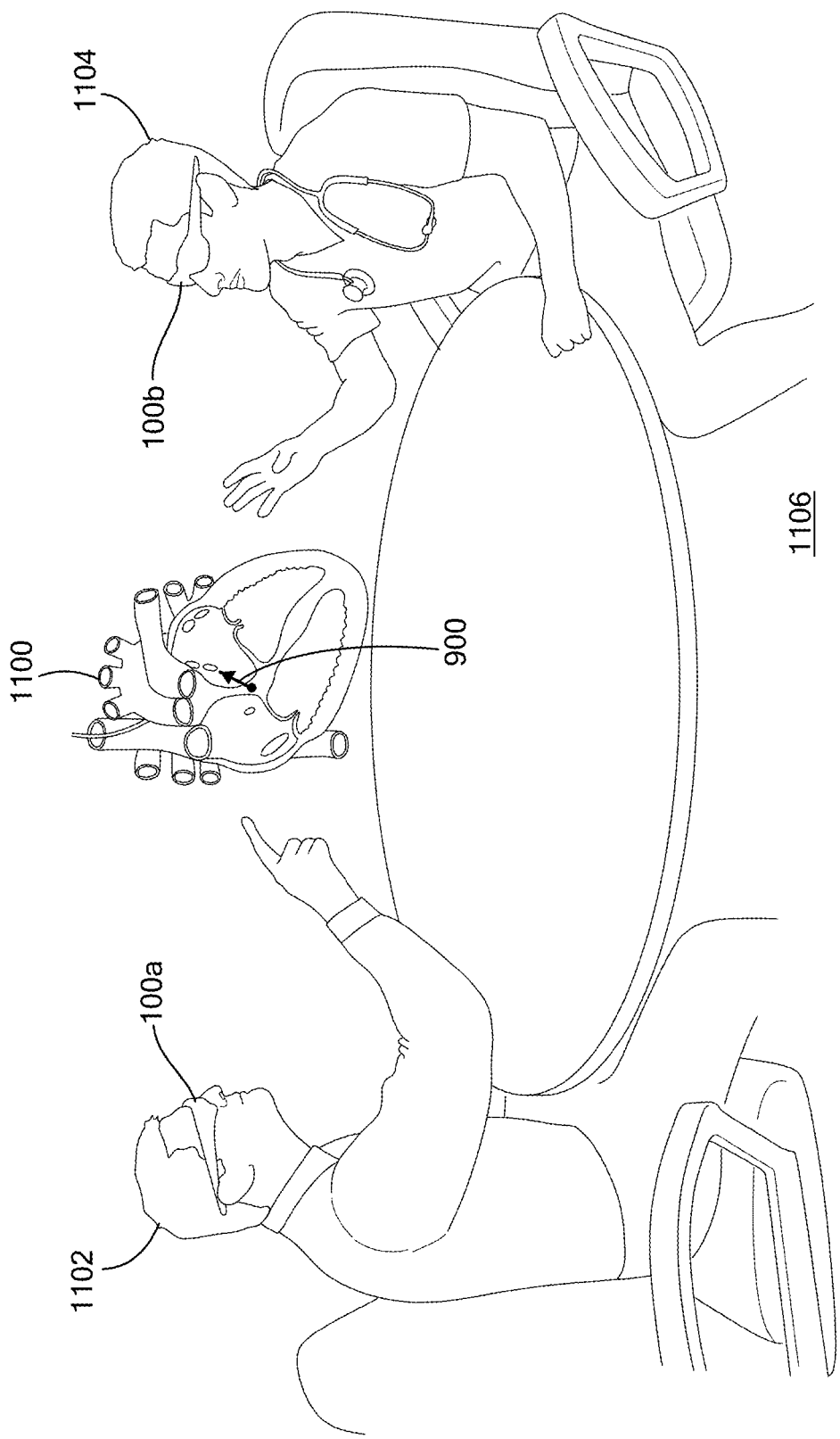
FIG. 11 illustrates a perspective view of an exemplary pre-operative planning room with each physician wearing the augmented reality device of FIG. 1 and viewing a free-floating virtual heart object in accordance with an embodiment of the present disclosure.
Figure 12:
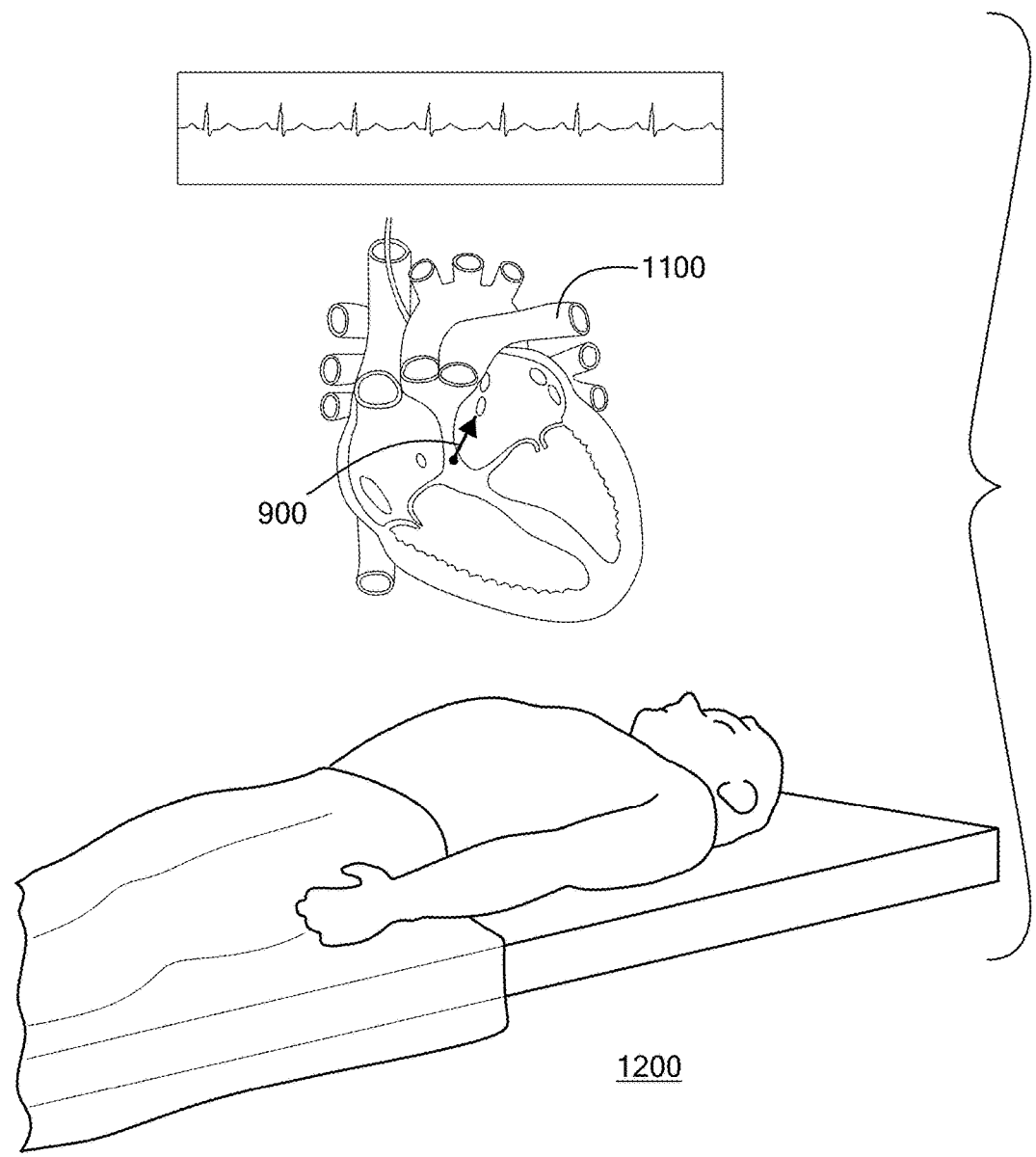
FIG. 12 illustrates an example of a physician's augmented reality view, via the augmented reality device of FIG. 1 (not shown), in a surgical room viewing a real-world patient on an operating table simultaneously with the free-floating virtual heart object of FIG. 11 in accordance with an embodiment of the present disclosure.
Figure 13:
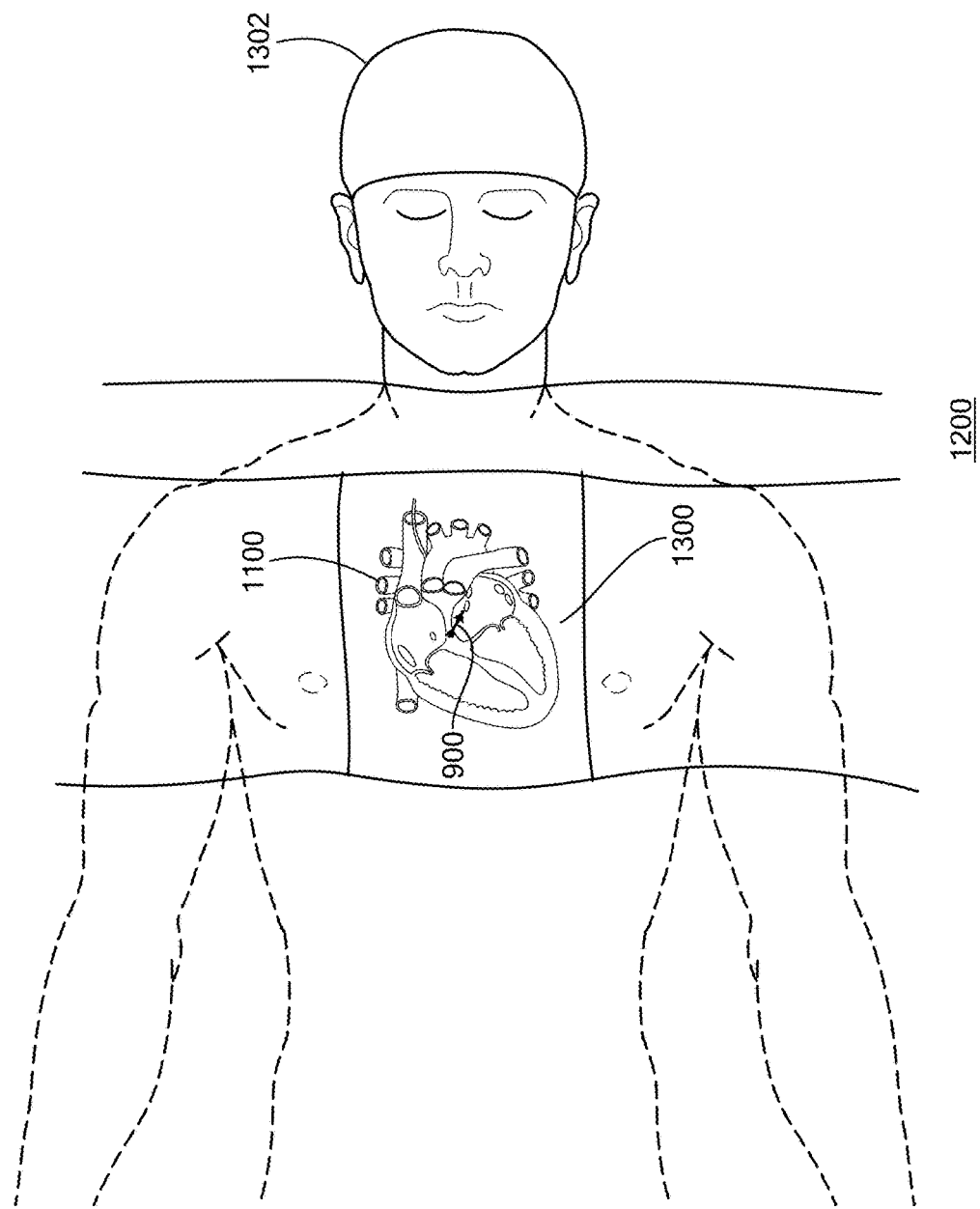
FIG. 13 illustrates an example of the physician's augmented reality view peering down on the real-world patient of FIG. 12, with the virtual heart object of FIG. 11 attached to the real-world patient's heart during the surgical procedure in accordance with an embodiment of the present disclosure.

For the LS 608 and LI 606 PVs, the data shows that the angles are fairly similar across the fossa ovalis locations 612', 612", 612''', with the LI PV generally having a more acute angle as compared to the LS PV angles. Also, the LI 606 distance is generally shorter than the LS 608 distances across the fossa ovalis locations 612', 612", 612'''. Such data can be extremely useful for assisting physicians with pre-operative planning for such cardiac procedures, as well as, for intraoperative guidance during such procedures. In one embodiment, the selected puncture location 612 and/or the trajectories 900 from the selected puncture location 612 to the target treatment areas (e.g., PVs) may be rendered/displayed on the virtual organ object 1100 (via the augmented reality device 100) in order to provide visual target guidance to the physician(s), as can be seen, for example, in FIG. 9. This may provide the physician with visual guidance for septal puncturing, as well as, steering the treatment device 400 within the patient's anatomy. Specifically, in addition to locating an optimal puncture location, the physician may use the visual target guidance of the trajectories 900 to steer the balloon 800 from the puncture 700 to the one or more target PVs 604, 606, 608, or 610. Such guidance may be provided during the pre-operative planning phase (as depicted in FIG. 11) and/or during the medical procedure (as depicted in FIGS. 12 and 13).

Although Tables 1 and 2 herein above show distance and angle values, additional embodiments of the present invention may also provide for additional information including, without limitation, location, curvature, and reach of the puncture device, catheter, or other treatment devices. It is contemplated that a variety of types of information may be used by, for example, the augmented reality device 100 to suggest candidate puncture locations and trajectories to the user.

In further embodiments, a trajectory of the one or more post-puncture treatment devices or other secondary devices may also be displayed via the augmented reality device 100, as described with reference to the trajectory of the puncturing device described herein above. In embodiments, the trajectory of the puncturing device may be displayed simultaneously with the post-puncture treatment devices or other secondary devices so that each combination of trajectories can be considered when selecting one or more of the trajectories. In some embodiments, each trajectory may be simultaneously viewable via the augmented reality device 100 and/or may be individually selectable as viewable by the user so that the user can select a subset less than all of the trajectories to view via the augmented reality device 100. As an example, trajectories of each of a catheter, a cryoballoon, a sheath, etc. may be displayable via the augmented reality device 100 simultaneously together and may also be selectively viewable such that the user can select one or more of the trajectories to not be displayed.

In other embodiments, a tissue thickness in the area of the septum may be displayed via the augmented reality device 100. In yet further embodiments, a depth of one or more lesions may be displayed via the augmented reality device 100 to assist users with, for example, lesion assessment. In yet other embodiments, anatomical structures adjacent to a target treatment and/or target puncture area, such as, for example, an aorta or a left bundle may be displayed via the augmented reality device 100 so that the user may beneficially select a trajectory, a movement path, or a position to avoid or maneuver around such adjacent anatomical structures. As one example, with a surgical valve procedure, a location of a suture may be displayed via the augmented reality device 100 so as to avoid contacting a conductive structure.

Figure 14:
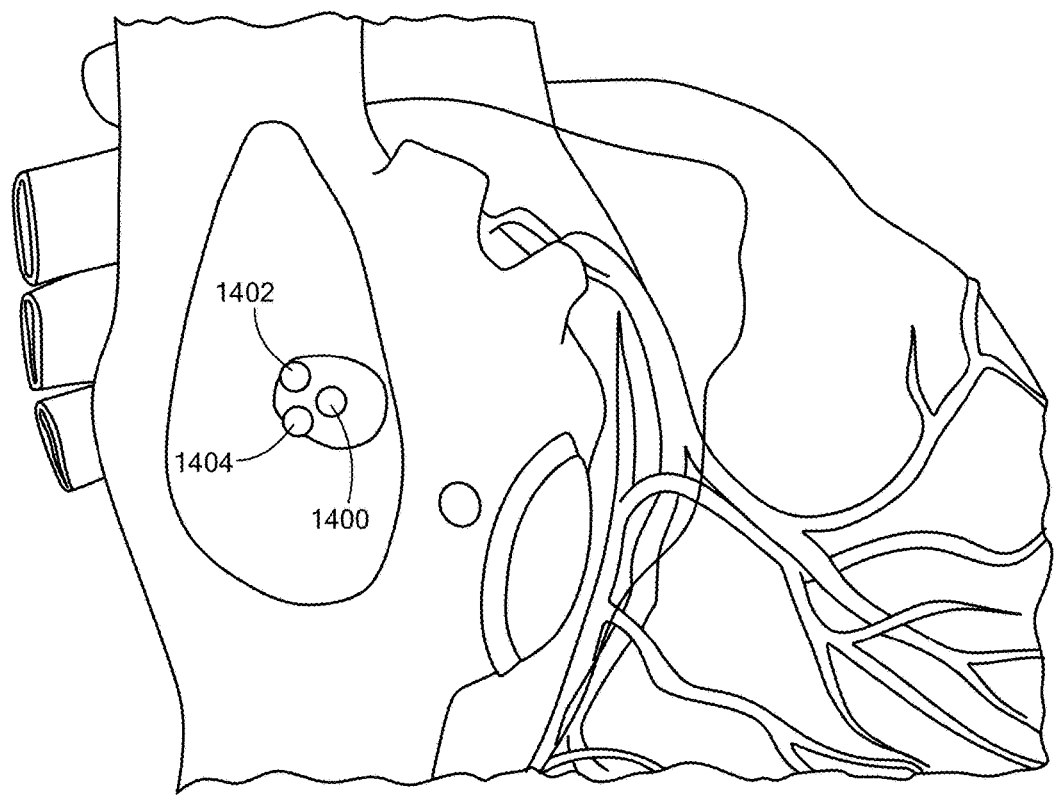
FIG. 14 illustrates a plurality of exemplary septal puncture locations for a plurality of medical devices based on the medical therapy or treatment being performed in accordance with embodiments of the present disclosure.

Other exemplary cardiac procedures may be enhanced/benefited by embodiments of the present invention. Specifically, several medical treatment devices require a septal puncture at specific location to optimize the device efficacy. Other such treatment devices are the left atrial appendage (LAA) closure device 1600 (for stroke prevention) and a mitral clip (for mitral valve regurgitation). FIG. 14 illustrates exemplary ideal puncture locations 1400, 1402, 1404 based on the particular medical device/treatment procedure. Specifically, the puncture location 1400 may be considered ideal for the mitral clip; the puncture location 1402 may be considered ideal for PVI; and the puncture location 1404 may be considered ideal for the LAA closure device 1600.

Figure 15:
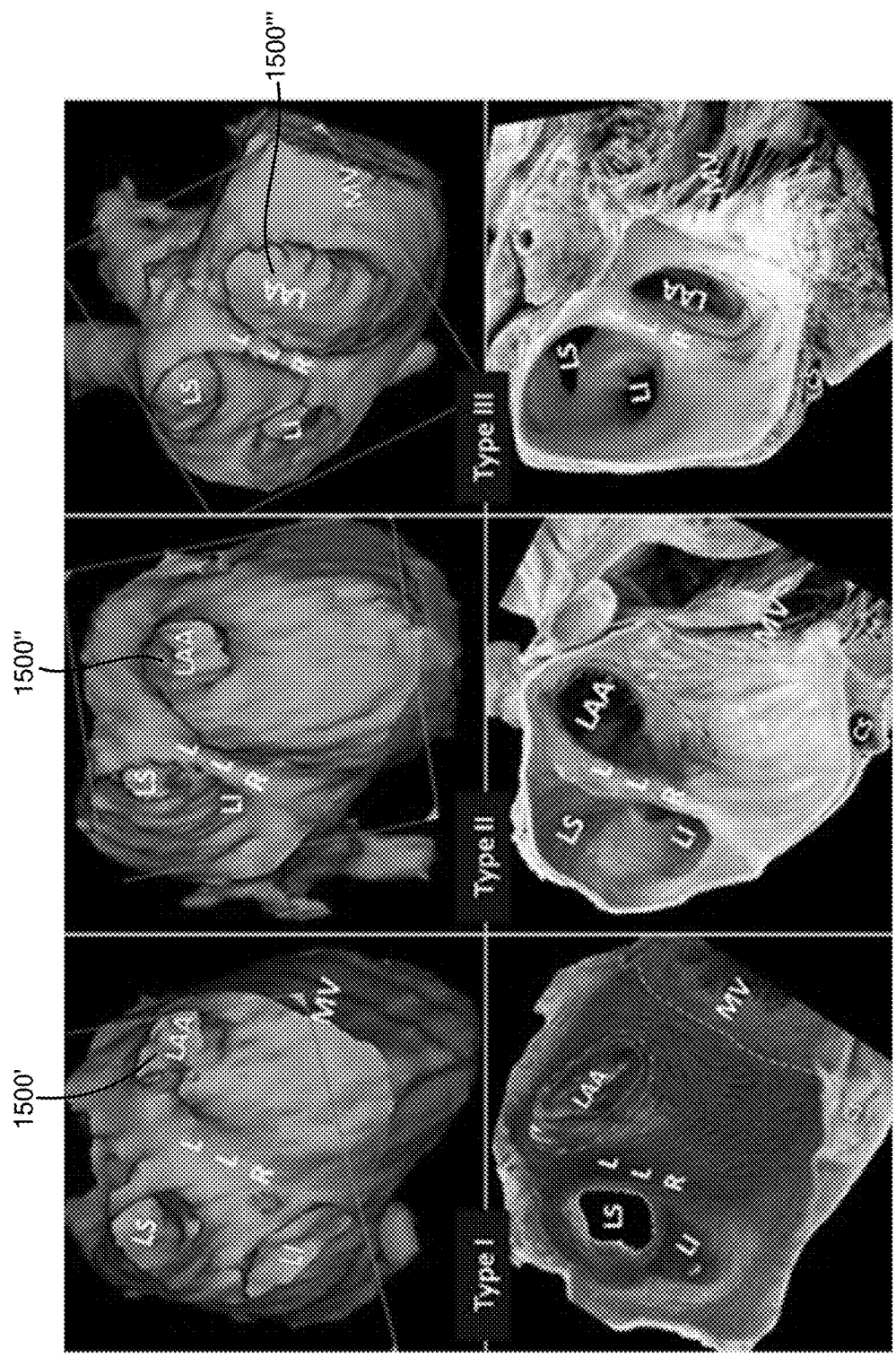
FIG. 15 illustrates a plurality of example left atrial appendage (LAA) locations and orientations that necessitate different septal puncture locations and medical device trajectories in accordance with embodiments of the present disclosure.

For example, the septal puncture location 1404 for the LAA closure device 1600 may be considered to be critical to the approach angle, sizing, and seating of the LAA closure device 1600. In fact, the shape, size, and location of the LAA 1602 within various patients is so highly variable that medical companies offering LAA closure devices 1600 to treat the LAA 1602 (e.g., LifeTech) can have as many as seventeen (17) different LAA closure device offerings. FIG. 15 is provided to further emphasize this point—it shows a plurality of examples of LAA locations 1500', 1500", 1500''' and orientations within different patients' hearts, which may warrant significantly different puncture locations and medical device trajectories. FIG. 16 illustrates an example of an idea septal puncture location 1604 and trajectory 1606 to optimally seat the LAA closure device 1600. Visual guides, such as, colored lines, dots, dotted lines, arrows, shapes, and the like may be rendered on the virtual organ object 1100 to guide the physician using the augmented reality device 100 according to embodiments of the present disclosure.

Referring now again primarily to the flow chart in FIG. 5, in step 508, the puncture location 700 may be selected based on the positional data, such as, for example, as discussed above with reference to the data from Tables 1 and 2. The puncture location 700 may be selected based on positional data of the target treatment anatomy (e.g., the pulmonary vein 604, the LAA 1602) of the patient relative to a position of the ancillary treatment anatomy (e.g., the fossa ovalis 612) of the patient, which may be determined from an analysis of the three-dimensional model of the patient's heart. Stated another way, the puncture location 700 may be selected based on the computer-generated trajectory from a location on the fossa ovalis 612 (e.g., superior, inferior, or center locations) to the target treatment anatomy.

As discussed herein above, a plurality of candidate puncture locations may be identified and trajectories (including distance and angle data, for example) determined from the plurality of candidate locations to the target treatment anatomy. The puncture location 700 may be selected, for example, based on a comparison of values (e.g., angle and/or distance) associated with the candidate trajectories (superior, center, and inferior fossa ovalis locations), as discussed herein above. For example, the superior fossa ovalis puncture location 612' may be selected due to having the largest angle value, as compared to the angle values for the center and inferior fossa ovalis candidate locations 612" and 612'". In one embodiment, a computing device, such as the augmented reality device 100, or another computing device in communication with the augmented reality device, may automatically select an optimal puncture location based on, for example, the rules discussed. In an alternative embodiment, the physician may select or change the optimal puncture location via, for example, user input into a user input interface 208. In some embodiments, the various candidate locations and trajectories may be stored on the memory 212 of the device 100 and the physician may select from among the locations and trajectories on-the-fly during the surgical procedure in order to, for example, scroll through the visual target guides on the virtual organ object 1100. In yet further embodiments, the candidate locations and trajectories are stored in a database (e.g., a cloud database) and may be selectively accessible and displayable by the user via the augmented reality device 100 during the procedure, or for use during other procedures.

Figure 9:
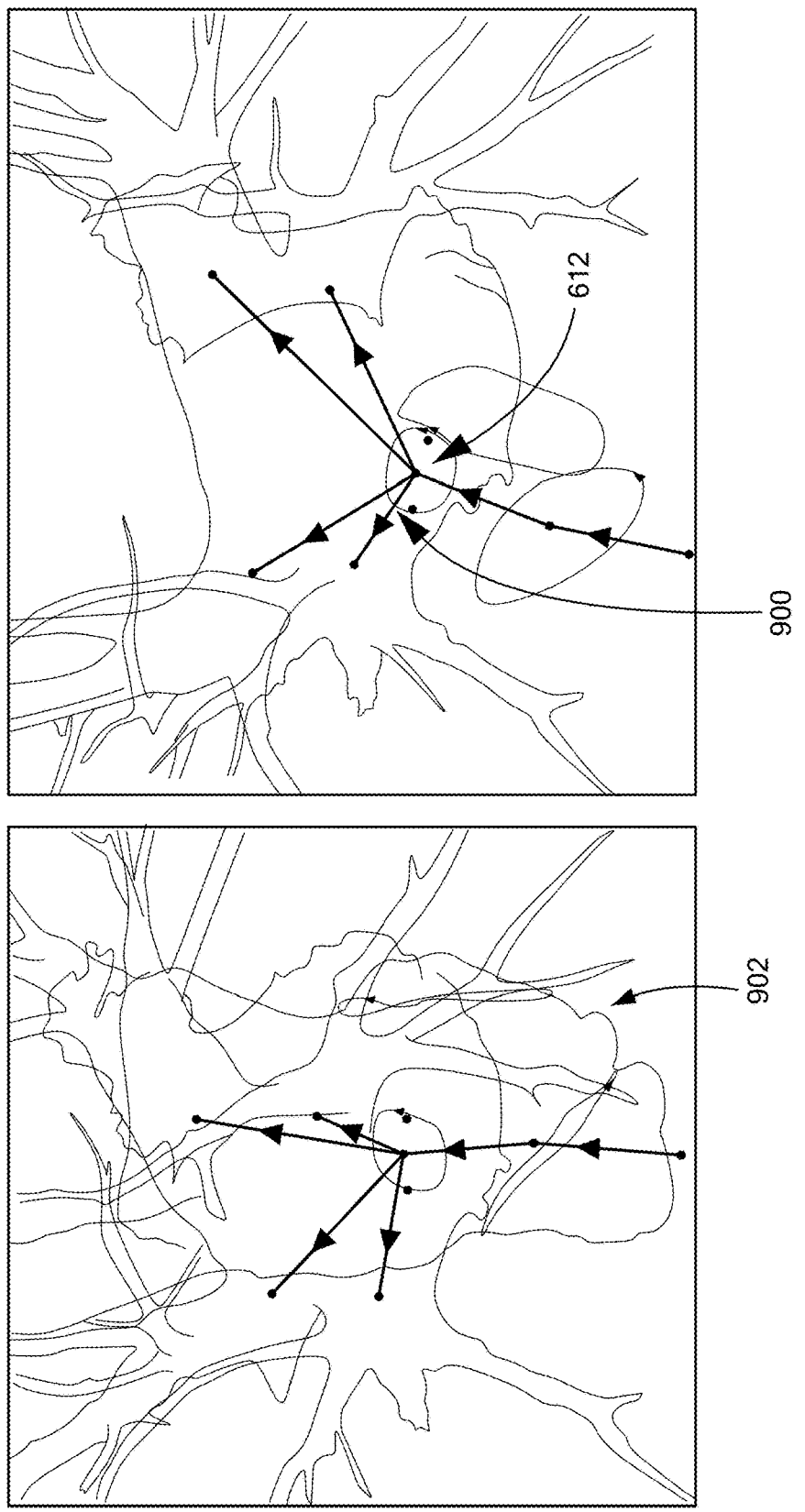
FIG. 9 illustrates exemplary trajectories of the catheter of FIG. 4 to the pulmonary veins based on the septal puncture location in accordance with embodiments of the present disclosure.

In step 510, the virtual organ object 1100 may be created based on the 3D model of the patient's heart. The virtual organ object 1100 may be based on a cross-section of the 3D model of the patient's heart, the cross-section being a cross-section that reveals the target treatment anatomy and the ancillary target anatomy of the patient for the medical procedure. Preferably, the virtual organ object 1100 should provide a visual indication or visual guide of the selected puncture location (and/or candidate locations) and/or the trajectories for guiding traversal of the treatment device 400 from the selected puncture location to the target treatment anatomy. FIG. 9 shows an example of the visual guides that may be provided on the virtual organ object 1100.

The visual guides may be provided in any graphical form, such as, for example, colored lines, arrows, or the like. For example, the visual guides may be formed as a traceable line, or may visually resemble real-world objects, such as the treatment device 400, for a more immersive experience.

The virtual organ object 1100 may be considered a 3D rendering of the patient's heart based on the pre-operative image data and the visual guides collectively. In one embodiment, the virtual organ object 1100 may be formed as a 3D hologram object provided by the augmented reality device 100 and viewable by the user 1102 or 1104 through the see-through display as a hologram augmenting the user's real-world view, as depicted in FIGS. 11-13. FIG. 11 illustrates a pre-op planning room 1106 where physicians may use the virtual organ object 1100 to discuss and plan the directional approach and therapy delivery of cardiac devices using embodiments of the present invention. FIGS. 12-13 show an example of the user's 1102 or 1104 field of view in a medical procedure room 1200. As can be seen in FIGS. 11-13, embodiments of the present disclosure may provide a mixed reality environment where virtual objects, such as, for example the virtual organ object 1100, may be rendered by the augmented reality device 100 and may, in some embodiments, interact with or be responsive to real objects in the field of view of the user 1102 or 1104. In some embodiments, one or more of the medical practitioners observing or participating in a medical procedure or in pre-op planning of the medical procedure in accordance with embodiments of the present disclosure may be avatars of real-world medical practitioners viewable via the augmented reality device 100.

In step 512, the virtual organ object 1100 may be displayed by the augmented reality device 100, overlaying a real-world environment 1106, 1200, as seen by the user 1102, 1104 through the lenses 104, 106 of the device 100. Stated another way, the real-world environment 1106 or 1200 may be considered simultaneously viewable by the user 1102 or 1104 of the device 100 via the augmented reality display system 200. For example, FIG. 12 shows the virtual organ object 1100 floating in free-space in the surgical room 1200 and FIG. 13 shows the virtual organ object 1100 being attached to and overlaying the patient's heart.

A variety of methods, devices, and techniques for using the augmented reality device 100 to display and/or attach the virtual organ object 1100 to a real-world object, such as the patient's anatomy 1300, may be used in embodiments of the present disclosure. For example, in one embodiment, the augmented reality display system 200 may be an optical see-through head-mounted display that places optical combiners directly in front of the user's eyes. The optical combiners are partially transmissive to permit the user 1102 (or 1104; however, only reference number 1102 may be used for simplicity) to see the real-world through the combiners. The combiners are also partially reflective to permit the user 1102 to see the virtual objects bounced off of the combiners. In another embodiment, the augmented reality display system 200 may use waveguides to display the virtual organ object 110 overlaying the user's real-world field of view. Other known techniques for using the augmented reality device 100 to overlay the virtual organ object 1100 with the user's real-world field of view may be used in embodiments of the present disclosure.

In some embodiments, the virtual organ object 1100 may cover a portion of the user's real-world field of view (see FIG. 13 for example where the patient's chest is covered by the virtual organ object 1100). In other embodiments, the virtual organ object 1102 may be semi-transparent such that the portion of the user's real-world view that would be covered is still viewable by the user 1102 beneath the virtual organ object 1100. As used herein, the term "overlay" is intended broadly to encompass both such embodiments where parts of the real-world are covered and where such parts are still viewable by the user beneath a semi-transparent virtual object.

In addition, the term "real-world environment" and "real-world object" are intended to indicate the physical world; in other words, the physical environment and physical objects therein. An example of a real-world environment is the surgical room 1200. Of course, as the user 1102 moves around the real-world environment viewable through the lenses 104, 106 changes. In other words, real-world objects may move in and out of the user's 1102 field of view as the user 1102 move about.

Accordingly, the virtual organ object 1100 may be configured to move with the movement of the user 1102 so that the virtual organ object 1100 is continuously within the user's 1102 field of view as the user 1102 moves about his/her environment. Alternatively, in some embodiments, as in step 514, the augmented reality device 100 may be configured to attach (also referred to in the AR field as "register") the virtual organ object 1100 to a physical object, such as the patient's anatomy 1300 (e.g., heart or chest), as seen in FIG. 13. When the virtual organ object 1100 is attached/registered to the patient's anatomy 1300, a movement of the user 1102 away from the patient's anatomy 1300

(e.g., the physician leaves the surgical room 1200) results in the virtual organ object 1100 moving out of the user's 1102 field of view. In other words, to provide a look-and-feel of virtual objects interacting with real-world objects, the device 100 may be configured to attach the virtual objects to real-world objects. This may enhance the physician's immersive experience with the virtual organ object 1102.

In some embodiments, the device 100 may be configured to allow the user 1102 to provide a user input selecting between an attachment mode and a non-attachment mode. In further embodiments, the device 100 may configured to allow the user 1102 to provide a user input selecting a real-world object to attach the virtual organ object 1100. In yet other embodiments, the device 100 may be configured to provide these features as default non-selectable features. Advantageously, by allowing the physician to view the visual guides within his/her field of view during the medical procedure, the physician may not be required to rely on existing heads-up monitors that require the physician to constantly look away from the patient 1302 in the surgical room 1200.

As used herein, the terms "surgeon" and "physician" are used interchangeably and are intended to indicate a medical practitioner. Further, the terms "surgical room" and "medical procedure room" may be used interchangeably and are intended to indicate an area or a room within which the medical/surgical procedure (e.g., PV occlusion, ablation, LAA closure, etc.) are or will be performed, as the case may be.

In addition, sensor data from the puncturing system 300, the control unit 304, and/or the catheter treatment device 400 may be displayable by the augmented reality device 100 within the physician's field of view, overlaying the real-world environment. Data such as, for example, temperature readings, pressure, electrical properties, and the like may be displayed by the device 100 in real-time during the procedure in order to assist the physician with being provided a real-time assessment of the efficacy of the procedure so that the physician can adjust his/her approach on-the-fly, as warranted.

A variety of known techniques for registering a virtual object may be used with embodiments of the present invention. For example, in one embodiment, outward-facing video cameras disposed on, or embedded within the augmented reality device 100 may capture video of the user's view of the real-world environment. The video data may be analyzed by the processors 210 to identify real-world objects in the user's field of view. Accordingly, the virtual organ object 1100 may be rendered based on a location of the identified real-world objects (e.g., patient). Movement of the real-world object may also be tracked by the cameras and the processors 210 such that the movements of the virtual organ object 1100 can be mapped to the movement of the real-world object. Embodiments of the present disclosure may use existing augmented reality devices, such as, for example, Microsoft's hololens. Aspects of the present disclosure may include software code (or other computer-executable instructions, e.g., the cardiac augmented reality module 202) configured to use the device 100 to identify a real-world patient, overlay the virtual organ object 1100 created based on the patient's pre-operative image data, and/or register the virtual organ object 1100 to the patient's anatomy 1300.

In a further embodiment, in step 516, a movement of the treatment device 400 during surgery may be tracked. Known techniques for tracking movement or identifying a position of a medical device within a patient's heart may be used with embodiments of the present disclosure. Such techniques include, for example, the use of radiographically opaque contrast medium to enable radiographic-mapping of the target tissue, the use of intra-operative video image data (e.g., endoscope), other intra-operative sensors (e.g., the pressure sensor 326) on the treatment device 400, and the like. Data from intra-operative imaging techniques can be used to track movement of the treatment device 400 within the patient's heart. In a preferred embodiment, a real-time movement of the treatment device 400 is tracked. In yet a further embodiment, the tracked movement of the treatment device 400, in step 518, is displayed on the virtual organ object 1100 during the surgical procedure to provide the physician with real-time feedback of the position of the medical device 500 relative to the target treatment anatomy. The tracked movement of the medical device 500 may be displayed on the virtual organ object 1100 similar to the visual guides for the selected puncture location and trajectories (e.g., lines, arrows, shapes, etc.), with the exception that the graphical representation of the tracked movement should be tied to the intracardiac movement of the treatment device 400.

Systems, devices, and methods for an augmented reality solution to optimize the directional approach and therapy delivery of interventional cardiology tools have been described herein. It should be understood that while embodiments of the present disclosure were described in the context of certain intracardiac medical procedures, the techniques described herein may also be useful with other medical devices and procedures in other embodiments of the present disclosure.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

In the above description, it should be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Further, unless otherwise indicated, terms such as "first", "second", "third" and so on are only used for descriptive purposes, and should not be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

What is claimed is:

1. A method of enhancing a surgical procedure, the method comprising:
providing a three-dimensional model of a heart of a patient based on image data of the heart of the patient;
identifying positional data corresponding to a first position of at least one target treatment anatomy of the patient relative to a second position of an ancillary target anatomy of the patient based on an analysis of the three-dimensional model of the heart of the patient;
selecting a puncture location based on the identified positional data of the at least one target treatment anatomy of the patient relative to the second position of an ancillary target anatomy of the patient, selecting the puncture location further comprising:
identifying a first candidate puncture location and a second candidate puncture location;
determining a first trajectory from the first candidate puncture location to the at least one target treatment anatomy and a second trajectory from the second candidate puncture location to the at least one target treatment anatomy;
selecting the puncture location based on a comparison of at least a first value associated with the first trajectory and at least a second value associated with the second trajectory; and
visually indicating one of the first trajectory and the second trajectory associated with the selected puncture location together with the visual indication of the selected puncture location on the virtual organ object being displayed in the displaying step, and
displaying, by an augmented reality device with an augmented reality display system, a virtual organ object via the augmented reality display system overlaying a real-world environment, the virtual organ object corresponding to the three-dimensional model of the heart of the patient and visually indicating the selected puncture location, each of the virtual organ object and at least a portion of the real-world environment being simultaneously viewable by a user of the augmented reality display system via the augmented reality display system.

2. The method in accordance with claim 1, wherein:
the real-world environment and the virtual organ object are simultaneously viewable within a single field of view of the user via the augmented reality display system.

3. The method in accordance with claim 1, wherein:
the positional data is associated with a computer-generated trajectory of a medical device from the ancillary target anatomy to the at least one target treatment anatomy; and
the medical device includes one of a catheter and a left atrial appendage closure.

4. The method in accordance with claim 1, wherein:
the at least a first value of the first trajectory and the at least a second value of the second trajectory being compared include at least one of an angle and a distance associated with the first trajectory and the second trajectory respectively.

5. The method in accordance with claim 1, wherein:
the visual indication of the one of the first trajectory and the second trajectory associated with the selected puncture location includes a line following a path of the one of the first trajectory and the second trajectory.

6. The method in accordance with claim 1, wherein:
the user is a medical practitioner;
the real-world environment is a surgical room for operating on the patient; and
the displaying is performed during a surgical procedure within the surgical room.

7. The method in accordance with claim 1, wherein:
the image data includes pre-operative image data of the heart of the patient, the pre-operative image data being associated with at least one of an MRI, an x-ray, an ultrasound, a fluoroscopy, an electrocardiogram, electroanatomical mapping, and a CT scan of the heart of the patient.

8. The method in accordance with claim 1, further comprising:
tracking in real-time a movement of the heart of the patient during a surgery; and
attaching the virtual organ object being displayed via the augmented reality display system with the tracked movement of the heart during the surgery.

9. The method in accordance with claim 1, further comprising:
tracking in real-time an intracardiac movement of a medical device within the heart of the patient during a surgery; and
displaying a visual indication of the tracked intracardiac movement of the medical device on the virtual organ object being displayed during the surgery via the augmented reality display system.

10. The method in accordance with claim 9, wherein:
the visual indication of the tracked intracardiac movement of the medical device is simultaneously viewable via the augmented reality display system with the visual indication of the selected puncture location.

11. The method in accordance with claim 1, further comprising:
determining a cross-sectional view of the heart of the patient to display in the displaying step, the displaying step further including displaying the determined cross-sectional view of the heart as the virtual organ object via the augmented reality display system.

12. The method in accordance with claim 1, further comprising:
receiving a user-selection of a surgical procedure to be performed on the heart of the patient; and
determining a cross-sectional view of the heart of the patient to display in the displaying step based on the user-selection of the surgical procedure to be performed on the heart of the patient, the displaying step further including displaying the determined cross-sectional view of the heart as the virtual organ object via the augmented reality display system.

13. The method in accordance with claim 1, wherein:
the ancillary target anatomy is a fossa ovalis and the at least one target treatment anatomy is one of a pulmonary vein and a left atrial appendage.

14. The method in accordance with claim 13, wherein the selecting the puncture location further includes:
selecting the puncture location based on a computer-generated trajectory from a location on the fossa ovalis to the one of the pulmonary vein and the left atrial appendage; and
the visual indication of the selected puncture location on the virtual organ object being displayed via the augmented reality display system includes a visual indication of the computer-generated trajectory.

* * * * *